(12) United States Patent
Lombardi et al.

(10) Patent No.: US 8,188,109 B2
(45) Date of Patent: May 29, 2012

(54) BENZOQUINOLIZINIUM SALT DERIVATIVES AS ANTICANCER AGENTS

(75) Inventors: Paolo Lombardi, Cesate (IT); Franco Buzzetti, Monza (IT); Andrea Guido Arcamone, Nerviano (IT)

(73) Assignee: Naxospharma S.r.l., Cesate (IT)

( * ) Notice: Subject to any disclaimer, the term of this patent is extended or adjusted under 35 U.S.C. 154(b) by 450 days.

(21) Appl. No.: 12/458,657

(22) Filed: Jul. 20, 2009

(65) Prior Publication Data

US 2011/0015222 A1  Jan. 20, 2011

(51) Int. Cl.
*A61K 31/4745* (2006.01)
*C07D 471/02* (2006.01)
(52) U.S. Cl. ............. 514/284; 546/71; 546/48; 514/280
(58) Field of Classification Search .................. 514/284, 514/280; 546/48, 56, 71
See application file for complete search history.

(56) References Cited

U.S. PATENT DOCUMENTS 6,008,356 A  12/1999  Kim et al.

FOREIGN PATENT DOCUMENTS

| EP | 2 070 926 A1 | 6/2009 |
| WO | WO 01/95908 A1 | 12/2001 |
| WO | WO 2009/002873 A1 | 12/2008 |

OTHER PUBLICATIONS

Gornall Karina C et al: "Selectivity of an indolyl berberine derivative for tetrameric G-quadruplex DNA", Rapid Communications in Mass Spectometry, vol. 21, No. 11, 2007.

*Primary Examiner* — Charanjit Aulakh
(74) *Attorney, Agent, or Firm* — Modiano & Associati; Albert Josif; Daniel O'Byrne

(57) ABSTRACT

13-substituted 5,6-dihydrodibenzo[a,g]quinolizinium salt compounds of the general formula (I):

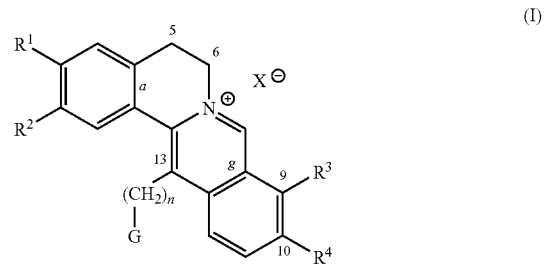

processes for the preparation of said compounds, pharmaceutical compositions containing said compounds and the use of said compounds for the manufacture of medicaments suitable for the treatment of cancerous diseases.

20 Claims, No Drawings

BENZOQUINOLIZINIUM SALT DERIVATIVES AS ANTICANCER AGENTS

The present invention relates to benzoquinolizinium salt derivatives and to processes for the preparation of said compounds. The invention also encompass pharmaceutical compositions containing said derivatives and the use of said compounds for the manufacture of medicaments suitable for the treatment of cancerous diseases.

BACKGROUND OF THE INVENTION

Protoberberines constitute a family of naturally occurring benzoquinolizinium alkaloids found in plants such as, for instance, Anonaceae, Berbiridaceae, Papaveraceae, Ranunculaceae. Relevant examples of protoberberines are Berberine or 9,10-dimethoxy-5,6-dihydrobenzo[g]-1,3-benzodioxolo[5,6-a]quinolizinium; Berberrubine (or Berbine) or 9-hydroxy-10-methoxy-5,6-dihydrobenzo[g]-1,3-benzodioxolo[5,6-a]quinolizinium; and Palmatine or 2,3,9,10-tetramethoxy-5,6-dihydrodibenzo[a,g]quinolizinium. The inventive benzoquinolizinium salt derivatives may be also considered and commonly termed as protoberberine derivatives. Both the scientific, IUPAC-recommended and the trivial, common nomenclatures will be used throughout the present specification interchangeably.

U.S. Pat. No. 3,910,938 and U.S. Pat. No. 3,920,665 disclose berbine compounds carrying alkyl, allyl or alkoxy substituents in position 13 as inhibitors of the growth of transplanted sarcoma strains in mice. There is no mention about additional (hetero)aromatic moieties linked to the substituents in position 13.

U.S. Pat. No. 6,008,356 and U.S. Pat. No. 6,030,978 disclose protoberberine derivatives substituted in position 13 by phenylmethyl (benzyl) and pyridylmethyl groups as antifungal agents, and pharmaceutical compositions containing them. Said patent specifications are completely silent in mentioning anything about an anticancer activity, and there is no reference about 13-(di)arylalkyl substituted compounds, even no disclosure or mention about phenylalkyl and pyridylalkyl substituents. Example 1 (13-benzyl) of said US patents was comparatively tested with the novel compounds of our specification, resulting in a much lower antitumour activity.

U.S. Pat. No. 6,239,139 and U.S. Pat. No. 6,255,317 disclose berberine derivatives bearing alkyl, alkenyl, cycloalkylalkyl, haloalkyl, ethoxycarbonyl, ethoxycarbonylmethyl, hydroxycarbonylmethyl, ethoxycarbonylethyl, and 2-valerolactonyl groups in position 13, as inhibitors of cholesterol biosynthesis. There is no mention about an antitumour activity and/or additional (hetero)aromatic moieties linked to the substituents in position 13.

WO 2008/040192 discloses berberine derivatives bearing lower alkyl, lower alkoxy and acetic acid lower alkyl esters in position 13. The said derivatives are glucose sorbefacient to muscle cells and have medical effects for improving glucose-tolerance and insulin-resistance, and can be used for treating diabetes mellitus, adiposity, fatty liver and their complications caused by insulin resistance. There is no mention about an antitumour activity and/or additional (hetero)aromatic moieties linked to the substituents in position 13.

Eur. J. Med. Chem., 31, 469, 1996 reports berberine analogues substituted in position 13 by solely unsubstituted lower alkyl groups as antibacterial agents.

Life Sciences 73, 1401, 2003 describes the effects of 13-methyl and 13-ethyl berberine on the expression of certain proteins in connection with a reported antibacterial activity.

Bioorg. Med. Chem. Lett. 16, 1707, 2006, discloses the compound 13-(piperidinopropyl) berberine and its binding to natural and synthetic G-quadruplex DNA structures.

Bioorg. Med. Chem. Lett. 19, 954, 2009, discloses various 13-alkyl and 13-benzyl 5,6-dihydrodibenzo[a,g]quinolizinium compounds as P2X$_7$ receptor antagonists as potential anti-inflammatory and immunomodulating agents.

J. Med. Chem, 52, 492, 2009 reports berberine analogues substituted in position 13 by solely lower alkyl and benzyl groups as LDL receptor up-regulators.

SUMMARY OF THE INVENTION

The present invention is concerned with 13-substituted 5,6-dihydrodibenzo [a,g]quinolizinium salt compounds of the general formula (I):

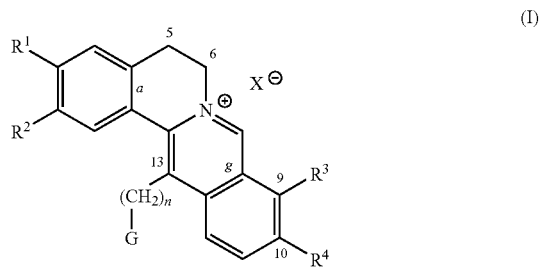

wherein
R$^1$ and R$^2$, which may be the same or different, represent independently a hydroxy or a (C$_1$-C$_6$)alkoxy group, or, taken together, a methylenedioxy group;
R$^3$ and R$^4$, which may be the same or different, represent independently a hydroxy or a (C$_1$-C$_6$)alkoxy group;
X represents inorganic acid ion, organic acid ion or halide;
n is an integer from 1 to 5 inclusive; and
G stands for
(a) —Z—Ar; or
(b) —Y=(Ar)$_2$
in which
Z is a bond, or O(CH$_2$)$_m$, CO—NH(CH$_2$)$_m$, or NH—CO (CH$_2$)$_m$;
Y is CH, O(CH$_2$)$_m$—CH, CO—N, CO—NH(CH$_2$)$_m$—CH, or NH—CO(CH$_2$)$_m$—CH;
m is an integer from 0 to 3 inclusive; and
Ar represents a 5-15 membered unsaturated or aromatic mono-, bi- or tricyclic carbocyclic or heterocyclic ring system, wherein any of said heterocyclic ring systems, for each occurrence, contains one o more heteroatoms selected from O, N, or S; and wherein any of said ring systems, for each occurrence, optionally contains from 1 to 4 substituents independently selected from halogen, cyano, nitro, hydroxy, amino, (di)(C$_1$-C$_6$)alkylamino, (C$_1$-C$_6$)alkylcarbonylamino, (C$_1$-C$_6$)alkoxy, (C$_1$-C$_6$) alkylcarbonyloxy, (C$_1$-C$_6$)alkoxycarbonyl, (C$_1$-C$_6$) alkyl; and wherein any of said (C$_1$-C$_6$)alk* moieties, for each occurrence, contains from 1 to 4 halogen atoms independently chosen from F, Cl, Br and I.

DETAILED DESCRIPTION OF THE INVENTION

It was surprisingly found, and that is a fundamental characteristic of the present invention, that the 13-substituted protoberberines of formula (I), in contrast to the prior art compounds derived from protoberberine structure, show a remarkable antitumour activities in relevant cancer cell lines. Accordingly, it can be expected that their applicability will encompass the treatment of several cancerous disorders, including cancers which are resistant to currently used anticancer agents.

According to a first object of the present invention there are provided 13-substituted 5,6-dihydrodibenzo[a,g]quinolizinium salt compounds (13-substituted protoberberines) of the general formula (I):

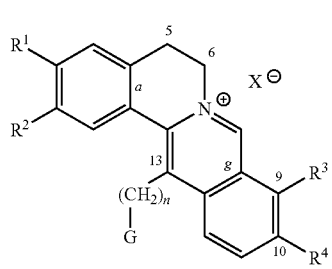

wherein $R^1$ and $R^2$, which may be the same or different, represent independently a hydroxy or a ($C_1$-$C_6$)alkoxy group, or, taken together, a methylenedioxy group;

$R^3$ and $R^4$, which may be the same or different, represent independently a hydroxy or a ($C_1$-$C_6$)alkoxy group;

X represents inorganic acid ion, organic acid ion or halide;
n is an integer from 1 to 5 inclusive; and
G stands for
(a) -Z—Ar; or
(b) —Y=(Ar)$_2$
in which
Z is a bond, or O(CH$_2$)$_m$, CO—NH(CH$_2$)$_m$, or NH—CO(CH$_2$)$_m$;
Y is CH, O(CH$_2$)$_m$—CH, CO—N, CO—NH(CH$_2$)$_m$—CH, or NH—CO(CH$_2$)$_m$—CH;
m is an integer from 0 to 3 inclusive; and Ar represents a 5-15 membered unsaturated or aromatic mono-, bi- or tricyclic carbocyclic or heterocyclic ring system, wherein any of said heterocyclic ring systems, for each occurrence, contains one o more heteroatoms selected from O, N, or S; and wherein any of said ring systems, for each occurrence, optionally contains from 1 to 4 substituents independently selected from halogen, cyano, nitro, hydroxy, amino, (di)($C_1$-$C_6$)alkylamino, ($C_1$-$C_6$)alkylcarbonylamino, ($C_1$-$C_6$)alkoxy, ($C_1$-$C_6$)alkylcarbonyloxy, ($C_1$-$C_6$)alkoxycarbonyl, ($C_1$-$C_6$)alkyl; and wherein any of said ($C_1$-$C_6$)alk* moieties, for each occurrence, contains from 1 to 4 halogen atoms independently chosen from F, Cl, Br and I.

Particularly, the invention relates to compounds of formula (I), wherein:

$R^1$ and $R^2$ are methoxy groups, or, taken together, represent a methylenedioxy group;
$R^3$ is hydroxy or methoxy;
$R^4$ is methoxy; and
X, n, and G are as defined above.

A first aspect of the invention relates to such compounds of formula (I), wherein:
G stands for -Z—Ar; and
Z and Ar are as defined above.

In one embodiment of the first aspect, the invention relates to such compounds wherein:
Z is a bond; and
n is 1, 2, 3, 4, or 5

In another embodiment of the first aspect, the invention relates to such compounds wherein:
Z is O(CH$_2$)$_m$;
m is 0, 1, or 2; and
n is 1, 2, or 3.

In yet another embodiment of the first aspect, the invention relates to such compounds wherein:
Z is CO—NH(CH$_2$)$_m$, or NH—CO(CH$_2$)$_m$;
m is 0, 1, or 2; and
n is 1.

In a second aspect, the invention relates to such compounds of formula (I), wherein:
G stands for —Y=(Ar)$_2$; and
Y and Ar are as defined above.

In one embodiment of the second aspect, the invention relates to such compounds wherein:
Y is CH; and
n is 1, 2, 3, or 4.

In another embodiment of the second aspect, the invention relates to such compounds wherein:
Y is O(CH$_2$)$_m$—CH;
m is 0 or 1; and
n is 1, 2 or 3.

In yet another embodiment of the second aspect, the invention relates to such compounds wherein:
Y is CO—N; and
n is 1.

In yet another embodiment of the second aspect, the invention relates to such compounds wherein:
Y is CO—NH(CH$_2$)$_m$—CH, or NH—CO(CH$_2$)$_m$—CH;
m is 0 or 1; and
n is 1.

In the compounds of formula (I), Ar can represent an unsaturated or aromatic mono- or bicyclic carbocyclic ring system radical chosen from phenyl, naphthyl, indenyl, azulenyl, optionally containing from 1 to 4 substituents.

In the compounds of formula (I), Ar can also represent an unsaturated or aromatic mono- or bicyclic heterocyclic ring system radical chosen from imidazolyl, quinolyl, isoquinolyl, indolyl, indazolyl, pyridazyl, pyridyl, pyrrolyl, pyrazolyl, pyrazinyl, quinoxalyl, pyrimidinyl, pyridazinyl, furyl, thienyl, triazolyl, thiazolyl, tetrazolyl, benzofuranoyl, oxazolyl, benzoxazolyl, isoxazolyl, isothiazolyl, thiazolyl, thiadiazoyl, benzodioxolyl, optionally containing from 1 to 4 substituents.

In the compounds of formula (I), when G stands for —Z—Ar, Ar can also represent an unsaturated or aromatic tricyclic carbocyclic or heterocyclic ring system radical chosen from fluorenyl, anthracenyl, 5H-dibenzocycloheptenyl, 10,11-dihydro-5H-dibenzocycloheptenyl, xanthenyl, acridinyl, phenothiazinyl, phenoxazinyl, carbazolyl, optionally containing from 1 to 4 substituents.

The substituents of the Ar moiety can be independently selected from, but not limited to, groups such as methyl, ethyl, propyl, and the like; trifluoromethyl, trichloromethyl, tribromomethyl, 2,2,2-trifluoroethyl, 2,2,2-trichloroethyl, and the like; hydroxy, methoxy, ethoxy, 2,2,2-trichloroethoxy, acetoxy, trifluoroacetoxy, trichloroacetoxy, and the like; amino, (di)methylamino, (di)ethylamino, acetamido, trifluoroacetamido and the like; cyano, nitro, fluoro, chloro, iodo and bromo.

The compounds of the following list are preferred. The indicated meaning of the anion X should not be construed as limiting the specific compound claimed, since a definite X can be easily converted into a different X simply by carrying out metathesis reactions, e.g. the iodide of a compound of the general formula (I) may be converted into the chloride of the same compound of the general formula (I) by treatment with silver chloride (see e.g., *J. Nat. Prod.* 61, 1150, 1998). Therefore, by referring, for instance, to the chloride (or bromide, or iodide, etc.) salt of a specific 13-substituted 5,6-dihydrodibenzo[a,g]quinolizinium, the present invention encompass also any other salt of that specific 13-substituted 5,6-dihydrodibenzo[a,g]quinolizinium which can be obtained by the above mentioned metathesis reaction.

13-[2-(phenyl)ethyl]-9,10-dimethoxy-5,6-dihydrobenzo[g]-1,3-benzodioxolo[5,6-a]quinolizinium iodide;

13-[2-(4-chlorophenyl)ethyl]-9,10-dimethoxy-5,6-dihydrobenzo[g]-1,3-benzodioxolo[5,6-a]quinolizinium iodide;

13-[2-(4-methoxyphenyl)ethyl]-9,10-dimethoxy-5,6-dihydrobenzo[g]-1,3-benzodioxolo[5,6-a]quinolizinium iodide;

13-[2-(4-methylphenyl)ethyl]-9,10-dimethoxy-5,6-dihydrobenzo[g]-1,3-benzodioxolo[5,6-a]quinolizinium iodide;

13-[2-(4-fluorophenyl)ethyl]-9,10-dimethoxy-5,6-dihydrobenzo[g]-1,3-benzodioxolo[5,6-a]quinolizinium iodide;

13-[2-(4-bromophenyl)ethyl]-9,10-dimethoxy-5,6-dihydrobenzo[g]-1,3-benzodioxolo[5,6-a]quinolizinium iodide;

13-[2-(4-trifluoromethylphenyl)ethyl]-9,10-dimethoxy-5,6-dihydrobenzo[g]-1,3-benzodioxolo[5,6-a]quinolizinium iodide;

13-[2-(4-trifluoromethoxyphenyl)ethyl]-9,10-dimethoxy-5,6-dihydrobenzo[g]-1,3-benzodioxolo[5,6-a]quinolizinium iodide;

13-[2-(4-nitrophenyl)ethyl]-9,10-dimethoxy-5,6-dihydrobenzo[g]-1,3-benzodioxolo[5,6-a]quinolizinium iodide;

13-[2-(4-dimethylaminophenyl)ethyl]-9,10-dimethoxy-5,6-dihydrobenzo[g]-1,3-benzodioxolo[5,6-a]quinolizinium iodide;

13-[2-(4-acetylaminophenyl)ethyl]-9,10-dimethoxy-5,6-dihydrobenzo[g]-1,3-benzodioxolo[5,6-a]quinolizinium iodide;

13-[2-(4-ethoxycarbonylphenyl)ethyl]-9,10-dimethoxy-5,6-dihydrobenzo[g]-1,3-benzodioxolo[5,6-a]quinolizinium iodide;

13-[2-(naphth-1-yl)ethyl]-9,10-dimethoxy-5,6-dihydrobenzo[g]-1,3-benzodioxolo[5,6-a]quinolizinium iodide;

13-[2-(4-chloronaphth-1-yl)ethyl]-9,10-dimethoxy-5,6-dihydrobenzo[g]-1,3-benzodioxolo[5,6-a]quinolizinium iodide;

13-[2-(4-methoxynaphth-1-yl)ethyl]-9,10-dimethoxy-5,6-dihydrobenzo[g]-1,3-benzodioxolo[5,6-a]quinolizinium iodide;

13-[2-(4-nitronaphth-1-yl)ethyl]-9,10-dimethoxy-5,6-dihydrobenzo[g]-1,3-benzodioxolo[5,6-a]quinolizinium iodide;

13-[2-(4-ethoxycarbonylnaphth-1-yl)ethyl]-9,10-dimethoxy-5,6-dihydrobenzo[g]-1,3-benzodioxolo[5,6-a]quinolizinium iodide;

13-[2-(indol-3-yl)ethyl]-9,10-dimethoxy-5,6-dihydrobenzo[g]-1,3-benzodioxolo[5,6-a]quinolizinium iodide;

13-[2-(5-chloroindol-3-yl)ethyl)]-9,10-dimethoxy-5,6-dihydrobenzo[g]-1,3-benzodioxolo[5,6-a]quinolizinium iodide;

13-[2-(5-nitroindol-3-yl)ethyl]-9,10-dimethoxy-5,6-dihydrobenzo[g]-1,3-benzodioxolo[5,6-a]quinolizinium iodide;

13-[2-(5-methoxyindol-3-yl)ethyl]-9,10-dimethoxy-5,6-dihydrobenzo[g]-1,3-benzodioxolo[5,6-a]quinolizinium iodide;

13-[2-(5-ethoxycarbonylindol-3-yl)ethyl]-9,10-dimethoxy-5,6-dihydrobenzo[g]-1,3-benzodioxolo[5,6-a]quinolizinium iodide;

13-[3-(phenyl)propyl]-9,10-dimethoxy-5,6-dihydrobenzo[g]-1,3-benzodioxolo[5,6-a]quinolizinium iodide;

13-[3-(4-chlorophenyl)propyl]-9,10-dimethoxy-5,6-dihydrobenzo[g]-1,3-benzodioxolo[5,6-a]quinolizinium iodide;

13-[3-(4-fluorophenyl)propyl]-9,10-dimethoxy-5,6-dihydrobenzo[g]-1,3-benzodioxolo[5,6-a]quinolizinium iodide;

13-[3-(4-bromophenyl)propyl]-9,10-dimethoxy-5,6-dihydrobenzo[g]-1,3-benzodioxolo[5,6-a]quinolizinium iodide;

13-[3-(4-methylphenyl)propyl]-9,10-dimethoxy-5,6-dihydrobenzo[g]-1,3-benzodioxolo[5,6-a]quinolizinium iodide;

13-[3-(4-methoxyphenyl)propyl]-9,10-dimethoxy-5,6-dihydrobenzo[g]-1,3-benzodioxolo[5,6-a]quinolizinium iodide;

13-[3-(4-trifluoromethoxyphenyl)propyl]-9,10-dimethoxy-5,6-dihydrobenzo[g]-1,3-benzodioxolo[5,6-a]quinolizinium iodide;

13-[3-(4-trifluoromethylphenyl)propyl]-9,10-dimethoxy-5,6-dihydrobenzo[g]-1,3-benzodioxolo[5,6-a]quinolizinium iodide;

13-[3-(4-nitrophenyl)propyl]-9,10-dimethoxy-5,6-dihydrobenzo[g]-1,3-benzodioxolo[5,6-a]quinolizinium iodide;

13-[3-(4-dimethylaminophenyl)propyl]-9,10-dimethoxy-5,6-dihydrobenzo[g]-1,3-benzodioxolo[5,6-a]quinolizinium iodide;

13-[3-(4-acetamidophenyl)propyl]-9,10-dimethoxy-5,6-dihydrobenzo[g]-1,3-benzodioxolo[5,6-a]quinolizinium iodide;

13-[3-(4-ethoxycarbonylphenyl)propyl]-9,10-dimethoxy-5,6-dihydrobenzo[g]-1,3-benzodioxolo[5,6-a]quinolizinium iodide;

13-[3-(4-phenoxyphenyl)propyl]-9,10-dimethoxy-5,6-dihydrobenzo[g]-1,3-benzodioxolo[5,6-a]quinolizinium iodide;

13-[3-(naphth-1-yl)propyl]-9,10-dimethoxy-5,6-dihydrobenzo[g]-1,3-benzodioxolo[5,6-a]quinolizinium iodide;

13-[3-(4-chloronahth-1-yl)propyl]-9,10-dimethoxy-5,6-dihydrobenzo[g]-1,3-benzodioxolo[5,6-a]quinolizinium iodide;

13-[3-(4-methoxynaphth-1-yl)propyl]-9,10-dimethoxy-5,6-dihydrobenzo[g]-1,3-benzodioxolo[5,6-a]quinolizinium iodide;

13-[3-(4-nitronaphth-1-yl)propyl]-9,10-dimethoxy-5,6-dihydrobenzo[g]-1,3-benzodioxol[5,6-a]quinolizinium iodide;

13-[3-(4-carbethoxynaphth-1-yl)propyl]-9,10-dimethoxy-5,6-dihydrobenzo[g]-1,3-benzodioxolo[5,6-a]quinolizinium iodide;

13-(3-indolylpropyl)-9,10-dimethoxy-5,6-dihydrobenzo[g]-1,3-benzodioxolo[5,6-a]quinolizinium iodide;

13-[3-(5-chloroindol-3-yl)propyl]-9,10-dimethoxy-5,6-dihydrobenzo[g]-1,3-benzodioxolo[5,6-a]quinolizinium iodide;

13-[3-(5-nitroindol-3-yl)propyl]-9,10-dimethoxy-5,6-dihydrobenzo[g]-1,3-benzodioxolo[5,6-a]quinolizinium iodide;

13-[3-(5-methoxyindol-3-yl)propyl]-9,10-dimethoxy-5,6-dihydrobenzo[g]-1,3-benzodioxolo[5,6-a]quinolizinium iodide;

13-[3-(5-carbethoxyindol-3-yl)propyl]-9,10-dimethoxy-5,6-dihydrobenzo[g]-1,3-benzodioxolo[5,6-a]quinolizinium iodide;

13-[(1,4-benzodioxan-2-yl)methyl]-9,10-dimethoxy-5,6-dihydrobenzo[g]-1,3-benzodioxolo[5,6-a]quinolizinium chloride;

13-[2,2-bis(phenyl)ethyl]-9,10-dimethoxy-5,6-dihydrobenzo[g]-1,3-benzodioxolo[5,6-a]quinolizinium iodide;

13-[2,2-bis(4-chlorophenyl)ethyl]-9,10-dimethoxy-5,6-dihydrobenzo[g]-1,3-benzodioxolo[5,6-a]quinolizinium iodide;

13-[2,2-bis(4-bromophenyl)ethyl]-9,10-dimethoxy-5,6-dihydrobenzo[g]-1,3-benzodioxolo[5,6-a]quinolizinium iodide;

13-[2,2-bis(4-fluorophenyl)ethyl]-9,10-dimethoxy-5,6-dihydrobenzo[g]-1,3-benzodioxolo[5,6-a]quinolizinium iodide;

13-[2,2-bis(4-methylphenyl)ethyl]-9,10-dimethoxy-5,6-dihydrobenzo[g]-1,3-benzodioxolo[5,6-a]quinolizinium iodide;

13-[2,2-bis(4-methoxyphenyl)ethyl]-9,10-dimethoxy-5,6-dihydrobenzo[g]-1,3-benzodioxolo[5,6-a]quinolizinium iodide;

13-[3,3-bis(phenyl)propyl]-9,10-dimethoxy-5,6-dihydrobenzo[g]-1,3-benzodioxolo[5,6-a]quinolizinium iodide;

13-[3,3-bis(4-methylphenyl)propyl]-9,10-dimethoxy-5,6-dihydrobenzo[g]-1,3-benzodioxolo[5,6-a]quinolizinium iodide;

13-[3,3-bis(4-methoxyphenyl)propyl]-9,10-dimethoxy-5,6-dihydrobenzo[g]-1,3-benzodioxolo[5,6-a]quinolizinium iodide;

13-[3,3-bis(4-fluorophenyl)propyl]-9,10-dimethoxy-5,6-dihydrobenzo[g]-1,3-benzodioxolo[5,6-a]quinolizinium iodide;

13-[3,3-bis(4-chlorophenyl)propyl]-9,10-dimethoxy-5,6-dihydrobenzo[g]-1,3-benzodioxolo[5,6-a]quinolizinium iodide;

13-[3,3-bis(4-bromophenyl)propyl]-9,10-dimethoxy-5,6-dihydrobenzo[g]-1,3-benzodioxolo[5,6-a]quinolizinium iodide;

13-benzyloxymethyl-9,10-dimethoxy-5,6-dihydrobenzo[g]-1,3-benzodioxolo[5,6-a]quinolizinium iodide;

13-[2-(phenoxy)ethyl]-9,10-dimethoxy-5,6-dihydrobenzo[g]-1,3-benzodioxolo[5,6-a]quinolizinium iodide;

13-[2-(benzyloxy)ethyl]-9,10-dimethoxy-5,6-dihydrobenzo[g]-1,3-benzodioxolo[5,6-a]quinolizinium iodide;

13-[3-(phenoxy)propyl]-9,10-dimethoxy-5,6-dihydrobenzo[g]-1,3-benzodioxolo[5,6-a]quinolizinium iodide;

13-[(1,4-benzodioxan-2-yl)methyl]-9,10-dimethoxy-5,6-dihydrobenzo[g]-1,3-benzodioxolo[5,6-a]quinolizinium iodide;

13-[(4-chlorobenzyloxy)methyl]-9,10-dimethoxy-5,6-dihydrobenzo[g]-1,3-benzodioxolo[5,6-a]quinolizinium iodide;

13-[(4-methoxybenzyloxy)methyl]-9,10-dimethoxy-5,6-dihydrobenzo[g]-1,3-benzodioxolo[5,6-a]quinolizinium iodide;

13-[(4-dimethylaminobenzyloxy)methyl]-9,10-dimethoxy-5,6-dihydrobenzo[g]-1,3-benzodioxolo[5,6-a]quinolizinium iodide;

13-[(4-hydroxybenzyloxy)methyl]-9,10-dimethoxy-5,6-dihydrobenzo[g]-1,3-benzodioxolo[5,6-a]quinolizinium iodide;

13-[2-(p-chlorophenoxy)ethyl]-9,10-dimethoxy-5,6-dihydrobenzo[g]-1,3-benzodioxolo[5,6-a]quinolizinium iodide;

13-[2-(p-methoxyphenoxy)ethyl]-9,10-dimethoxy-5,6-dihydrobenzo[g]-1,3-benzodioxolo[5,6-a]quinolizinium iodide;

13-[2-(p-hydroxyphenoxy)ethyl]-9,10-dimethoxy-5,6-dihydrobenzo[g]-1,3-benzodioxolo[5,6-a]quinolizinium iodide;

13-[2-(p-chlorobenzyloxy)ethyl]-9,10-dimethoxy-5,6-dihydrobenzo[g]-1,3-benzodioxolo[5,6-a]quinolizinium iodide;

13-[2-(p-methoxybenzyloxy)ethyl]-9,10-dimethoxy-5,6-dihydrobenzo[g]-1,3-benzodioxolo[5,6-a]quinolizinium iodide;

13-[2-(p-hydroxybenzyloxy)ethyl]-9,10-dimethoxy-5,6-dihydrobenzo[g]-1,3-benzodioxolo[5,6-a]quinolizinium iodide;

13-[3-(p-chlorophenoxy)propyl]-9,10-dimethoxy-5,6-dihydrobenzo[g]-1,3-benzodioxolo[5,6-a]quinolizinium iodide;

13-[3-(p-methoxyphenoxy)propyl]-9,10-dimethoxy-5,6-dihydrobenzo[g]-1,3-benzodioxolo[5,6-a]quinolizinium iodide;

13-[3-(p-hydroxyphenoxy)propyl]-9,10-dimethoxy-5,6-dihydrobenzo[g]-1,3-benzodioxolo[5,6-a]quinolizinium iodide;

13-[2-(diphenylmethyloxy)ethyl]-9,10-dimethoxy-5,6-dihydrobenzo[g]-1,3-benzodioxolo[5,6-a]quinolizinium iodide;

13-diphenylmethyloxymethyl-9,10-dimethoxy-5,6-dihydrobenzo[g]-1,3-benzodioxolo[5,6-a]quinolizinium iodide;

13-benzylaminocarbonylmethyl-9,10-dimethoxy-5,6-dihydrobenzo[g]-1,3-benzodioxolo[5,6-a]quinolizinium iodide;

13-phenylaminocarbonylethyl-9,10-dimethoxy-5,6-dihydrobenzo[g]-1,3-benzodioxolo[5,6-a]quinolizinium iodide;

13-phenylaminocarbonylmethyl-9,10-dimethoxy-5,6-dihydrobenzo[g]-1,3-benzodioxolo[5,6-a]quinolizinium iodide;

13-[(4-pyridyl)aminocarbonylmethyl]-9,10-dimethoxy-5,6-dihydrobenzo[g]-1,3-benzodioxolo[5,6-a]quinolizinium iodide;

13-[(1-indolyl)carbonylmethyl)-9,10-dimethoxy-5,6-dihydrobenzo[g]-1,3-benzodioxolo[5,6-a]quinolizinium iodide;

13-[(p-chlorobenzyl)aminocarbonylmethyl]-9,10-dimethoxy-5,6-dihydrobenzo[g]-1,3-benzodioxolo[5,6-a]quinolizinium iodide;

13-[(p-methoxybenzyl)aminocarbonylmethyl]-9,10-dimethoxy-5,6-dihydrobenzo[g]-1,3-benzodioxolo[5,6-a]quinolizinium iodide;

13-[(p-dimethylaminobenzyl)aminocarbonylmethyl]-9,10-dimethoxy-5,6-dihydrobenzo[g]-1,3-benzodioxolo[5,6-a]quinolizinium iodide;

13-[(p-hydroxybenzyl)aminocarbonymethyl]-9,10-dimethoxy-5,6-dihydrobenzo[g]-1,3-benzodioxolo[5,6-a]quinolizinium iodide;

13-[(p-chlorophenyl)aminocarbonylmethyl]-9,10-dimethoxy-5,6-dihydrobenzo[g]-1,3-benzodioxolo[5,6-a]quinolizinium iodide;

13-[(p-methoxyphenyl)aminocarbonylmethyl]-9,10-dimethoxy-5,6-dihydrobenzo[g]-1,3-benzodioxolo[5,6-a]quinolizinium iodide;
13-[(p-dimethylaminophenyl)aminocarbonylmethyl]-9,10-dimethoxy-5,6-dihydrobenzo[g]-1,3-benzodioxolo[5,6-a]quinolizinium iodide;
13-[(p-hydroxyphenyl)aminocarbonylmethyl]-9,10-dimethoxy-5,6-dihydrobenzo[g]-1,3-benzodioxolo[5,6-a]quinolizinium iodide;
13-[(5-chloroindol-1-yl)carbonylmethyl]-9,10-dimethoxy-5,6-dihydrobenzo[g]-1,3-benzodioxolo[5,6-a]quinolizinium iodide;
13-[(5-methoxyindol-1-yl)carbonylmethyl]-9,10-dimethoxy-5,6-dihydrobenzo[g]-1,3-benzodioxolo[5,6-a]quinolizinium iodide;
13-[(5-hydroxyindol-1-yl)carbonylmethyl]-9,10-dimethoxy-5,6-dihydrobenzo[g]-1,3-benzodioxolo[5,6-a]quinolizinium iodide;
13-[(5-dimethylaminoindol-1-yl)carbonylmethyl]-9,10-dimethoxy-5,6-dihydrobenzo[g]-1,3-benzodioxolo[5,6-a]quinolizinium iodide;
13-benzylcarbonylaminomethyl-9,10-dimethoxy-5,6-dihydrobenzo[g]-1,3-benzodioxolo[5,6-a]quinolizinium iodide;
13-phenylcarbonylaminomethyl-9,10-dimethoxy-5,6-dihydrobenzo[g]-1,3-benzodioxolo[5,6-a]quinolizinium iodide;
13-[(4-pyridyl)carbonylaminomethyl]-9,10-dimethoxy-5,6-dihydrobenzo[g]-1,3-benzodioxolo[5,6-a]quinolizinium iodide;
13-[(p-chlorobenzyl)carbonylaminomethyl]-9,10-dimethoxy-5,6-dihydrobenzo[g]-1,3-benzodioxolo[5,6-a]quinolizinium iodide;
13-[(p-methoxybenzyl)carbonylaminomethyl]-9,10-dimethoxy-5,6-dihydrobenzo[g]-1,3-benzodioxolo[5,6-a]quinolizinium iodide;
13-[(p-hydroxybenzyl)carbonylaminomethyl]-9,10-dimethoxy-5,6-dihydrobenzo[g]-1,3-benzodioxolo[5,6-a]quinolizinium iodide;
13-[(p-chlorophenyl)carbonylaminomethyl]-9,10-dimethoxy-5,6-dihydrobenzo[g]-1,3-benzodioxolo[5,6-a]quinolizinium iodide;
13-[(p-methoxyphenyl)carbonylaminomethyl]-9,10-dimethoxy-5,6-dihydrobenzo[g]-1,3-benzodioxolo[5,6-a]quinolizinium iodide; and
13-[(p-hydroxyphenyl)carbonylaminomethyl]-9,10-dimethoxy-5,6-dihydrobenzo[g]-1,3-benzodioxolo[5,6-a]quinolizinium iodide.

According to a second object of the present invention, there are provided processes for the preparation of the compounds of the general formula (I).

A first process comprises reacting a 13-substituted tetrahydroprotoberberine of general formula (II)

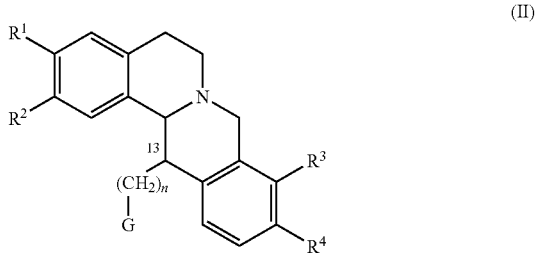

wherein $R^1$, $R^2$, $R^3$, $R^4$, G and n are as previously defined, with such oxidizing agents as represented by halogens, e.g. $Br_2$ or $I_2$, or haloamides and haloimides, e.g N-chloro-, N-bromo- or N-iodosuccinimide to give a compound of the general formula (I) wherein $R^1$, $R^2$, $R^3$, $R^4$, G and n are as previously defined, and X represents the halogen atom derived from the above oxidizing agent used, being said 13-substituted tetrahydroprotoberberines of the general formula (II) obtained as follow:

i) when G stands for -Z—Ar, wherein Z is a bond or $O(CH_2)_m$, or for —Y=(Ar)$_2$, wherein Y is CH or O(CH$_2$)$_m$—CH, reacting a dihydroprotoberberine of general formula (III)

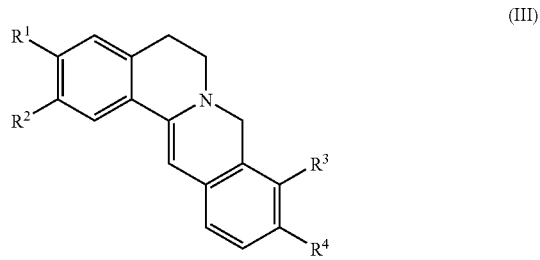

with an halide of general formulae (IVa) or (IVb)

$$Hal-(CH_2)_n-Z—Ar \quad (IVa)$$

$$Hal-(CH_2)_n—Y=(Ar)_2 \quad (IVb)$$

wherein:
$R^1$, $R^2$, $R^3$, $R^4$, Ar, n and m are as previously defined, Z and Y are as herein above stated, and Hal is an halogen atom such as chlorine, bromine and iodine, to give a 13-substituted iminiumprotoberberine derivative of formula (V)

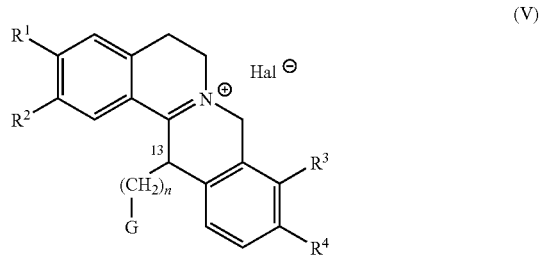

wherein $R^1$, $R^2$, $R^3$, $R^4$, n are as previously defined, and G is as herein above stated, and
reducing the 13-substituted iminiumprotoberberine of formula (V) to obtain a 13-substituted tetrahydroprotoberberine of the general formula (II-i)

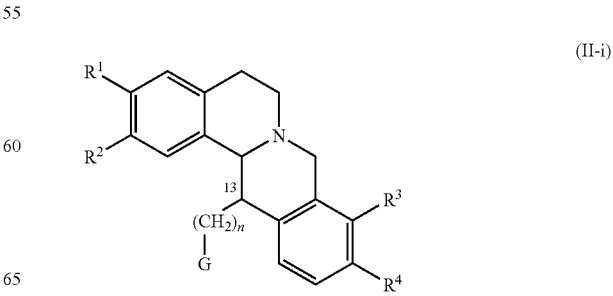

wherein $R^1$, $R^2$, $R^3$, $R^4$, n are as previously defined, and G is as herein above stated;

ii) when G stands for -Z—Ar, wherein Z is CO—NH$(CH_2)_m$, or for —Y=Ar)$_2$, wherein Y is CO—N or CO—NH$(CH_2)_m$—CH, reacting a dihydroprotoberberine of the general formula (III) with a haloalkanoic acid ester of formula (VI)

Hal-(CH)$_n$COOR$^5$     (VI)

wherein Hal and n are as previously defined, and $R^5$ represents such radicals as methyl, ethyl, t-butyl, benzyl, 2,2,2-trichloethyl and the like, to obtain an 13-alkylcarboxy acid ester iminiumprotoberberine derivative of formula (VII),

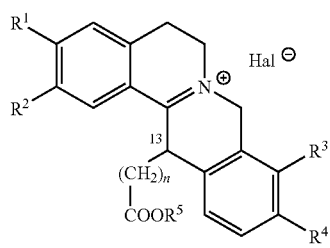

(VII)

reducing the 13-substituted iminiumprotoberberine of formula (VII) to obtain the tetrahydroprotoberberine of formula (VIII)

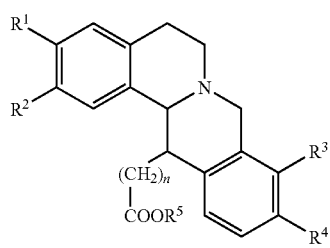

(VIII)

hydrolyzing or cleaving the ester group of the compound of formula (VIII) to obtain a 13-alkylcarboxy acid tetrahydroprotoberberine derivative of the general formula (IX)

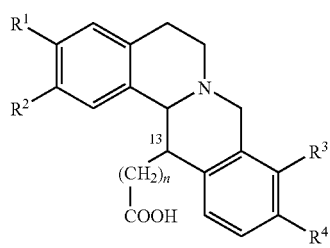

(IX)

subjecting the acid compound (IX) so obtained to an amidation reaction with an amine compound of formulae (X), (XI), or (XII)

H$_2$N(CH$_2$)$_m$—Ar     (X)

HN(Ar)$_2$     (XI)

H$_2$N(CH$_2$)$_m$—CH(Ar)$_2$     (XII)

wherein Ar and m are as previously defined to obtain a 13-substituted tetrahydroprotoberberine of the general formula (II-ii)

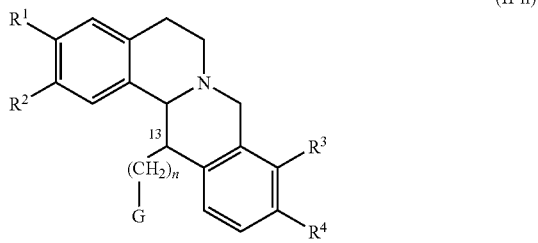

(II-ii)

wherein $R^1$, $R^2$, $R^3$, $R^4$, n are as previously defined, and G is as herein above stated;

iii) when G stands for -Z—Ar, wherein Z is NH—CO$(CH_2)_m$, or for —Y=(Ar)$_2$, wherein Y is CO—N or NH—CO$(CH_2)_m$—CH, obtaining the acyl azido derivative of formula (XIII)

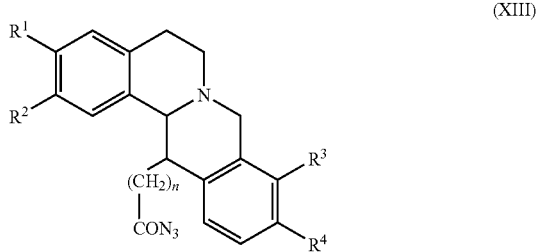

(XIII)

from the corresponding 13-alkylcarboxy acid tetrahydroprotoberberine derivative of the above general formula (IX), and subjecting the acyl azido derivative of formula (XIII) so obtained to a retro-amidation reaction with an acid compound of formulae (XIV), (XV), or (XVI)

HOOC(CH$_2$)$_m$—Ar     (XIV)

HOOCCH(Ar)$_2$     (XV)

HOOC(CH$_2$)$_m$—CH(Ar)$_2$     (XVI)

wherein Ar and m are as previously defined to obtain a 13-substituted tetrahydroprotoberberine of the general formula (II-iii)

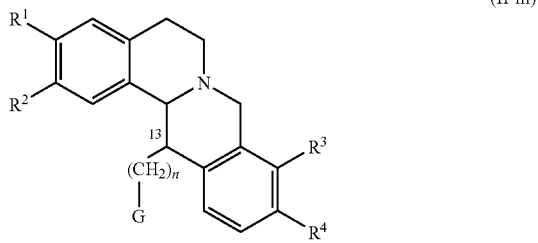

(II-iii)

wherein $R^1$, $R^2$, $R^3$, $R^4$, n are as previously defined, and G is as herein above stated.

The oxidation of a 13-substituted tetrahydroprotoberberine of general formula (II) to give the compounds of the invention, may be be carried out according to known methods, for instance as described in U.S. Pat. No. 6,030,978 or in *J. Nat. Prod.* 61, 115 (1998). The reaction may be performed in an organic solvent such as chloroform, ethanol or acetic acid at temperatures ranging from 0 to about 100° C. Preferably the reaction is carried out in chloroform at reflux when N-chlorosuccinimide or N-bromosuccinimide is used. When iodine is employed the preferred solvent is ethanol at reflux. The preferred solvent is acetic acid when bromine is used as oxidizing agent. Preferably the oxidation is carried out with N-chlorosuccinimide or iodine.

The reaction of a dihydroprotoberberine of general formula (III) with a halide of general formulae (IVa) or (IVb) to give a 13-substituted iminiumprotoberberine derivative of formula (V), wherein G stands for -Z—Ar, wherein Z is a bond or O(CH$_2$)$_m$, or for —Y=(Ar)$_2$, wherein Y is CH or O(CH$_2$)$_m$—CH, and the similar reaction of a dihydroprotoberberine of general formula (III) with a haloalkanoic acid ester of formula (VI) to give a 13-alkylcarboxy acid ester iminiumprotoberberine derivative of formula (VII), may be carried out as generally reported for enamine alkylations. The enamine alkylation, herebelow described, is an analogy process, for example as reported in *Bioorganic & Medicinal Chemistry Letters* 16, 3913 (2006). The alkylation may be performed in inert organic solvent, for instance acetonitrile, chloroform, dichloromethane or dioxane. Preferably the reaction is carried out in hot acetonitrile in the presence of sodium iodide. In the compounds of formula (IVa) and (IVb) the halogen atom is preferably bromine or iodine.

The compounds of general formulae (IVa), (IVb) or (VI) are commercially available or known from the literature, or can be prepared by modifications of known chemical procedures which are well within the ordinary skill of one practicing the art of organic synthesis.

Suitable reaction conditions for the reduction of the iminium compounds of formula (V) and (VII) to obtain the corresponding 13-substituted tetrahydroprotoberberine of formula (II-i) and (VIII), respectively, are sodium or potassium borohydride in a protic solvent, such as methanol, ethanol or isopropanol. Preferably the reduction is carried out in ethanol solution at room temperature using an excess of sodium borohydride. The hydrolysis or the cleavage of the ester group of the ester compound of formula (VII) to obtain a 13-alkylcarboxy acid tetrahydroprotoberberine derivative of formula (IX) may be performed following usual methods and procedures known in organic chemistry for the hydrolysis of methyl, ethyl, t-butyl esters or for the cleavage of benzyl and trichloroethyl esters, respectively.

The amidation reaction of a compound compound of formula (IX) with an amine of formulae (X), (XI) or (XII) to obtain a compound of general formula (II-i), wherein G stands for -Z—Ar, wherein Z is CO—NH(CH$_2$)$_m$, or for —Y=(Ar)$_2$, wherein Y is CO—N or CO—NH(CH$_2$)$_m$—CH is performed by usual procedures described in organic chemistry. Such condensation agents as dicyclohexylcarbodiimide or 1-(3-dimethylaminopropyl)-3-ethyl carbodiimide hydrochlorides can be used, as described, for instance, in *J. Amer. Chem. Soc.* 95, 875 (1973). As catalyst, dimethylaminopyridine may be used used. The reaction may be performed in an organic solvent such as dimethylformamide or dichlormethane, at temperatures ranging from 0° C. to about 50° C.

The amine compounds of general formulae (X), (XI) and (XII) are commercially available or known from the literature, or can be prepared by modifications of known chemical procedures which are well within the ordinary skill of one practicing the art of organic synthesis.

The retro-amidation reaction of an acyl azido derivative of formula (XIII) with an acid compound of formulae (XIV), (XV), or (XVI) to obtain a compound of general formula (II-iii), wherein G stands for -Z—Ar, wherein Z is NH—CO (CH$_2$)$_m$, or for —Y=(Ar)$_2$, wherein Y is CO—N or NH—CO (CH$_2$)$_m$—CH, is known to proceed through the intermediacy of a reactive isocyanate generated from the acyl azido derivative of formula (XIII) as a precursor (Curtius reaction). Suitable conditions for performing such a retro-amidation reaction are as reported, for instance, in Example 6 of WO92/09574. The acyl azido derivative of formula (XIII) is obtained by the corresponding acid of formula (IX) with methods known in organic chemistry. A preferred method is by the use of diphenyl phosphorazidate (DPPA), as described in *Tetrahedron*, 30, 2151, 1974.

The acid compounds of general formulae (XIV), (XV), or (XVI) are commercially available or known from the literature, or can be prepared by modifications of known chemical procedures which are well within the ordinary skill of one practicing the art of organic synthesis.

In a particular case of the inventive compounds of the general formula (I) where G stands for -Z—Ar, wherein Z is a bond or O(CH$_2$)$_m$, or for —Y=(Ar)$_2$, wherein Y is CH or O(CH$_2$)$_m$—CH, there is provided a second process for the preparation of the compounds of the invention comprising reacting a 8-acetonylprotoberberine of the general formula (XVII), obtained as described, for instance, in U.S. Pat. No. 6,255,317

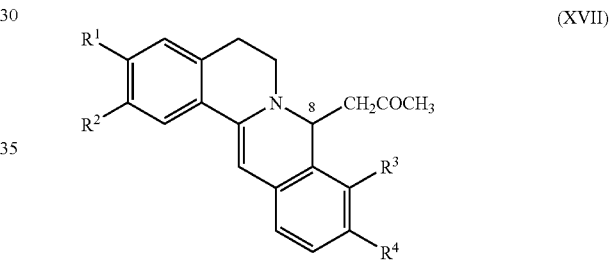

(XVII)

with an excess of the halide of the above described general formulae (IVa) or (IVb) to obtain a 13-substituted protoberberine derivative of the general formula (I) wherein R$^1$, R$^2$, R$^3$, R$^4$, and n are as previously described, G is as herein above stated, and X represents Hal in the above described general formulae (IVa) or (IVb). Usually, the reaction is performed in acetonitrile solution at temperatures ranging from room to reflux temperatures. Preferably, the halocompound of formulae (IVa) or (IVb) is used in a large excess (2-10 mol. eq.). When chloro or bromo compounds are used, generally 1-3 mol. eq. of an alkali metal iodide are added to accelerate the reaction.

According to a third object of the present invention there are provided pharmaceutical compositions containing, as active ingredient, a compound of formula (I) combined with a pharmaceutically acceptable diluent or carrier. Accordingly, a therapeutically effective dose of a compound of formula (I) is combined with an inert carrier. The compositions may be formulated in a conventional manner using common carriers as known to a person skilled in the pharmaceutical art. A preferred carrier is alpha-, beta- or gamma-cyclodextrin.

As stated, the invention is based on the surprising recognition that the 13-substituted protoberberines of formula (I), in contrast to the prior art compounds derived from protoberberine structure, show a considerable antitumour activities in relevant cancer cell lines. Such a unique anticancer profile has not so far been described in the patent and scientific literature in connection with any one of the prior art protoberberine derivatives.

For the determination of the in vitro antitumour activities, the compounds of the invention were assayed in a panel of sensible, resistant and refractory tumour cell lines, which are only exemplary for the antitumour activity of the inventive compounds, and are not to be construed as limiting their antitumour activities only to the cell lines set forth herein. Cell lines. The 2008 cell line was established from a patient with serous cystadenocarcinoma of the ovary and the cDDP-resistant C13* subline, about 15-fold resistant to cDDP, was derived from the parent 2008 cell line by monthly exposure to cDDP, followed by chronic exposure to step-wise increases in cDDP concentration (*Cancer Research* 52, 1895, 1992). The cell lines were grown as monolayers in RPMI 1640 medium containing 10% heat-inactivated fetal bovine serum and 50 µg/mL gentamycin sulfate. All cell media and serum were purchased from (Lonza, Verviers, Belgium). Cultures were equilibrated with humidified 5% $CO_2$ in air at 37° C. All studies were performed in Mycoplasma negative cells, as routinely determined with the MycoAlert Mycoplasma detection kit (Lonza, Walkersville, Md., USA).

The human ovarian cancer cell line A2780 and a platinum-resistant subline selected in vitro by stepwise increases of cisplatin concentration in the medium were from University of Modena and Reggio Emilia. The cisplatin resistant A2780 cells were challenged weekly with 50 uM cisplatin for 1 hr. Both cell lines were maintained in RPMI 1640 medium with 10% (vol/vol) fetal calf serum, penicillin (62.9 mg/L), and streptomycin (100 mg/L) (GIBCO).

Cell growth assay. Cell growth was determined by a modification of the crystal violet dye assay (*Analytical biochemistry*, 182, 16 1989). On selected days, after removal of the tissue culture medium, the cell monolayer was fixed with methanol prior to staining with 0.2% crystal violet solution in 20% methanol for at least 30 minutes. After washing several times with distilled water to remove the dye excess, the cells were let to dry. The incorporated dye was solubilized in acidic isopropanol (1N HCl : 2-propanol, 1:10). After appropriate dilution, dye was determined spectrophotometrically at 540 nm. The extracted dye was proportional to cell number. Percentage of cytotoxicity was calculated by comparing the absorbance of cultures exposed to the compounds of the invention to non-exposed (control) cultures. The data are shown in the following Tables 1a and 1b. Percentage of cytotoxicity is here reported as the half maximal inhibitory concentration (IC50), which is a measure of the effectiveness of a compound of the invention in inhibiting cell growth by half with respect to control (100%).

TABLE 1a

| Cell line | Compound IC50 (uM) at 72 hrs exposure | | | | | | | |
|---|---|---|---|---|---|---|---|---|
| | cDDP | 5-FU | Berberine | Comp Ex | NAX012 | NAX013 | NAX014 | NAX018 |
| 2008 | 3.6 | 10 | 10 | 9.2 | 3.6 | 6.6 | 5.8 | 4 |
| C13* | 17 | 8 | 6 | 5 | 2.2 | 2.4 | 1.8 | 0.66 |

TABLE 1b

| Cell line | Compound IC50 (uM) at 72 hrs exposure | | | | | | | |
|---|---|---|---|---|---|---|---|---|
| | cDDP | Berberine | Comp Ex | NAX012 | NAX013 | NAX014 | NAX018 | NAX030 |
| A2780 | 2 | 4 | 2.5 | 0.6 | 1 | 1.4 | 0.4 | 4.5 |
| A2780/CP | 20 | 2.5 | 3.3 | 0.6 | 1 | 1 | 1 | 2.5 |

Cell cultures and treatments. Human tumor cells (HeLa from uterin cervix and HCT116 from colon carcinoma) were grown at 37° C. in humidified atmosphere containing 5% $CO_2$ in D-MEM supplemented with 10% FCS, 4 mM glutamine, 2 mM Na pyruvate, 100 U/mL penicillin and 0.1 mg/mL streptomycin (all reagents were from Celbio, Pero, Italy). HeLa cells are the most widely used human tumor cell line; HCT 116 colon carcinoma cell line has proven to be extremely resistant to conventional chemotherapy. Cells were treated with the compounds of the invention at a fixed dose of 10 uM for 24 h, eventually followed by 24 of recovery in drug free medium. As a positive control of growth inhibition, cells were treated with 10 uM etoposide. Some of the inventive were also assayed at a dose of 1 uM.

Cell proliferation assays—MTT assay. Cells are seeded in 96 multiwell-plates at the density of $10^3/100$ µl (except fibroblasts that are seeded at the density of $1.5 \times 10^3/100$ µl). Cells are treated 24 h later with the drug for 24 h eventually followed by 24 h of recovery in drug-free medium. At the end of the treatments, 20 µl of *CellTiter 96 Non-Radioactive Cell Proliferation Assay* (*MTT*; Promega, Milano, Italy) are added to each well. Plates are then incubated for 4 h at 37° C. in the dark and analyzed with a reader of microplates (Gio. De Vita, Roma, Italy) at 492 nm. Experiments are performed in quadruplicate and repeated three times. Data are expressed in the following Tables 2a-c as the percentage compared to control cells considered as 100%.

TABLE 2a

| | Compound at 10 uM | | | | | | | |
|---|---|---|---|---|---|---|---|---|
| Cell line | Etoposide | Berberine | Comp Ex | NAX012 | NAX013 | NAX014 | NAX018 | NAX019 |
| HeLa | | | | | | | | |
| 24 h | 74.8 | 121.2 | 98.0 | 72.4 | 74.5 | 71.9 | 40.6 | 62.8 |
| 24 h + 24 h | 1.0 | 92.9 | 74.5 | 41.3 | 60.8 | 45.4 | 11.3 | 33.5 |
| HCT 116 | | | | | | | | |
| 24 h | 104.2 | 166.0 | 20.4 | 0.0 | 10.0 | 49.5 | 30.6 | 6.0 |
| 24 h + 24 h | 96.2 | 93.3 | 22.2 | 34.8 | 60.2 | 15.4 | 13.7 | 32.1 |

TABLE 2b

| | Compound at 1 uM | | | | |
|---|---|---|---|---|---|
| Cell line | Etoposide | Berberine | Comp Ex | NAX014 | NAX018 |
| HeLa | | | | | |
| 24 h | 94.3 | 178.3 | 139.1 | 92.1 | 64.0 |
| 24 h + 24 h | 59.5 | 168.3 | 93.6 | 59.4 | 45.8 |

TABLE 2c

| | Compound at 1 uM at 24 h exposure | | | | | |
|---|---|---|---|---|---|---|
| Cell line | Etoposide | Berberine | Comp Ex | NAX012 | NAX013 | NAX018 |
| HCT 116 | 138.8 | 201.1 | 119.4 | 52.1 | 58.1 | 68.2 |

Legend to Tables cDDP: cisplatin; cis-diaminedichloroplatinum

5-FU: fluorouracil; 5-fluoro-2,4(1H,3H)-pyrimidinedione

Etoposide: VP16; 4'-demethylepipodophyllotoxin 9-[4,6-O-ethylidene-beta-D-glucopyranoside]

Berberine: 9,10-dimethoxy-5,6-dihydrobenzo[g]-1,3-benzodioxolo[5,6-a]quinolizinium chloride Comp Ex: 13-benzyl-9,10-dimethoxy-5,6-dihydrobenzo[g]-1,3-benzodioxolo[5,6-a]quinolizinium iodide NAX012: 13-(3-phenylpropyl)-9,10-dimethoxy-5,6-dihydrobenzo[g]-1,3-benzodioxolo[5,6-a]quinolizinium iodide NAX013: 13-[2-(4-methoxyphenyl)ethyl]-9,10-dimethoxy-5,6-dihydrobenzo[g]-1,3-benzodioxolo[5,6-a]quinolizinium iodide NAX014: 13-[2-(4-chlorophenyl)ethyl]-9,10-dimethoxy-5,6-dihydrobenzo[g]-1,3-benzodioxolo[5,6-a]quinolizinium iodide NAX018: 13-(3,3-diphenylpropyl)-9,10-dimethoxy-5,6-dihydrobenzo[g]-1,3-benzodioxolo[5,6-a]quinolizinium iodide NAX019: 13-[2-(indol-3-yl)ethyl]-9,10-dimethoxy-5,6-dihydrobenzo[g]-1,3-benzodioxolo[5,6-a]quinolizinium iodide NAX030: 13-[(5-chloroindol-1-yl)carbonylmethyl]-9,10-dimethoxy-5,6-dihydrobenzo[g]-1,3-benzodioxolo[5,6-a]quinolizinium iodide Accordingly, the claimed compounds are useful for the therapeutic treatments of tumour diseases in humans and other mammals by administration of therapeutically effective quantities of the compound of formula (I) to a subject under treatment for, e. g., leukemias, lymphomas, solid tumours such as sarcomas, breast, ovarian, and cervical carcinomas, bladder and prostate carcinomas, bronchogenic, gastric and hepatic carcinomas, mesotheliomas, brain tumours, glioblastoma and the like. The claimed compounds and compositions and may be administered alone or in combination with one or more additional chemotherapeutic or growth inhibitory agents. Examples of chemotherapeutic agents include alkylating agents such as thiotepa and cyclosphosphamide; alkyl sulfonates such as busulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK(R); razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel and docetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin.

Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

Various delivery systems are known and can be used to administer an agent of the invention, e.g., encapsulation in liposomes, microparticles, microcapsules. Methods of introduction can be enteral or parenteral and include but are not limited to intradermal, intramuscular, intraperitoneal, intravenous, subcutaneous, intranasal, intraocular, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be daily, weekly, or monthly, or in combination with other agents. Pulmonary administration can also be employed, e.g., by use of an inhaler or nebulizer, and formulation with an aerosolizing agent. The amount of the inventive compound that will be effective for its intended therapeutic use can be determined by standard clinical techniques based on the present description. In addition, in vitro assays may optionally be employed to help identify optimal dosage ranges. Generally, suitable dosage ranges for intravenous administration are generally about 1-50 mg/kg body weight, preferably about 5-40 mg/kg body weight, most preferably about 10-20 mg/kg body weight.

The following examples illustrate the invention without limiting its scope.

PREPARATIVE EXAMPLE 1

9,10-Dimethoxy-5,8-dihydro-6H-benzo[g]-1,3-benzodioxolo[5,6-a]quinolizine (Dihydroberberine)

To a solution of berberine hydrochloride (3,718 g, 10 mmol) in pyridine (30 mL) was added portionwise sodium borohydride (450 mg, 12 mmol) and the mixture was stirred at room temperature for 30 min. More sodium borohydride (380 mg, 10 mmol) was added and stirring was continued for 1 h. The reduction was monitored by TLC (DCM-ethyl acetate-methanol 4:4:2). The mixture was poured onto ice water. The precipitate was filtered, the residue washed with water and then dried under vacuum over calcium chloride to give 2.860 g of title compound in about 85 % yield.

NMR (200 MHz, CDCl$_3$): δ 2.87 (t, J=5.8 Hz, 2H), 3.12 (t, J=5.9 Hz, 2H), 3.84(s, 6H), 4.31 (br s, 2H), 5.94 (s, 2H), 5.95 (s, 1H), 6.58 (brs, 1H), 6.74 (s, 2H), 7.16 (s, 1H).

PREPARATIVE EXAMPLE 2

8-Acetonyl-9,10-dimethoxy-5,8-dihydro-6H-benzo[g]-1,3-benzodioxolo[5,6-a]quinolizine (8-Acetonyl-dihydroberberine)

Berberine chloride (3.718 g, 10 mmol) was dissolved in 5N sodium hydroxide solution (17 mL, 85 mmol) at room temperature. Then acetone (3.7 mL, 2.90 g, 50 mmol) was added dropwise and the mixture stirred for about 6 h at room temperature. The reaction was monitored by TLC (hexane-diethylamine 9:1). The precipitate was filtered, washed with methanol 80% to neutral pH and then dried under vacuum to give 3.020 g of a white solid (80% yield).

NMR (200 MHz, DMSO-d$_6$): δ 2.03 (s, 3H), 2.30 (dd, J=4.8/14.4 Hz, 1H), 2.74 (m, 2H), 2.93 (dd, J=6.6/14.4 Hz, 1H), 3.24 (m, 3H), 3.76 (s, 3H), 3.77 (s, 3H), 5.21 (dd, J=4.8/6.6 Hz, 1H), 5.99 (s, 2H), 6.00 (s, 1H), 6.72 (d, J=8.4, 1H), 6.75 (s, 1H), 6.86 (d, J=8.4 Hz, 1H), 7.24 (s, 1H)

PREPARATIVE EXAMPLE 3

(9,10-Dimethoxy-5,8,13,13a-tetrahydro-6H-benzo[g]-1,3-benzodioxolo[5,6-a]quinolizin-13-yl)-acetic acid ethyl ester (13-ethoxycarbonylmethyl-tetrahydroberberine)

Dry ethyl bromoacetate (30 mL, 270.5 mmol) was added dropwise with stirring to dihydroberberine (2.62 g, 0.78 mmol) at 0° C. under a nitrogen atmosphere. The solution was heated to 100° C. for 1 h to give a suspension. Dry toluene (25 mL) was added to the suspension, the precipitate filtered and then dried to give the unstable iminium salt intermediate (3.78 g, 8.9 mmol) which was dissolved in absolute ethanol (50 mL) and stirred at 0° C. Sodium borohydride (400 mg, 10.5 mmol) was added to the suspension which was then stirred at room temperature for 20 min. More sodium borohydride (400 mg, 10.5 mmol) was added and further stirred for 1 h. The mixture was then concentrated by solvent evaporation in vacuo. Water (200 mL) was added to the crude product and the mixture then extracted with diethyl diethyl ether (3×150 mL). The combined diethyl ether extract was washed with water, dried and evaporated. The crude product was chromotographed on silica gel eluting with dichloromethane to afford the ethyl ester of (9,10-dimethoxy-5,8,13,13a-tetrahydro-6H-benzo[g]-1,3-benzodioxolo[5,6-a]quinolizin-13-yl)-acetic acid as a yellow solid (2.8 g, 88% yield).

m.p. 103-104° C.

NMR (300 Mz, CDCl$_3$): δ 1.15 (t, J=7.2 Hz, 3H), 2.30 (dd, J=15.6, 8.4 Hz, 1H), 2.44 (dd, J=15.6, 8.4 Hz, 1H), 2.50-2.61 (m, 2H), 2.99-3.13 (m, 2H), 3.52 (d, J=16 Hz, 1H), 3.61-3.68 (m, 1H), 3.72 (br s, 1H), 3.85 (s, 6H,), 3.98 (q, J=7 Hz, 2H), 4.10 (d, J=16 Hz, 1H), 5.91 (d, J=1.3 Hz, 1H), 5.92 (d, J=1.3 Hz, 1H), 6.58 (s, 1H), 6.74 (s, 1H), 5.76 (d, J=8.4 Hz, 1H), 7.00 (d, J=8.4 Hz, 1H).

By proceeding analogously and starting from the appropriate haloalknoic acid ethyl ester of formula (VI), the following compounds were obtained:
(9,10-Dimethoxy-5,8,13,13a-tetrahydro-6H-benzo[g]-1,3-benzodioxolo[5,6-a]quinolizin-13-yl)-propionic acid ethyl ester (13-ethoxycarbonylethyl-tetrahydroberberine).

PREPARATIVE EXAMPLE 4

(9,10-Dimethoxy-5,8,13,13a-tetrahydro-6H-benzo[g]-1,3-benzodioxolo[5,6-a]quinolizin-13-yl)-acetic acid (13-carboxymethyl-tetrahydroberberine)

To a solution of the ethyl ester compound of Preparative Example 3 (372 mg, 0.88 mmol) in methanol (20 mL) was added a 2% aqueous solution of lithium hydroxide (30 mL) and the mixture heated for 1 h at reflux. The reaction mixture was evaporated, water was added and then acidified to pH 1 with 1N HCl. The precipitate was filtered, washed with water and dried to afford the title compound as a white solid (334 mg, 95%).
m.p. 202-205° C.
NMR (300 MHz, CDCl$_3$): δ 2.59-2.85 (m, 4H), 3.18-3.34 (m, 2H), 3.42-3.50 (m, 1H), 3.73 (d, J=15.6 Hz, 1H), 3.87 (s, 3H), 3.88 (s, 3H), 4.06 (d, J=3.3 Hz, 1H), 4.32 (d, J=15.6 Hz, 1H), 5.98 (s, 2H), 6.60 (s, 1H), 6.64 (s, 1H), 6.86 (d, J=8.7 Hz, 1H), 7.00 (d, J=8.7 Hz, 1H).
By proceeding analogously the following compounds were obtained:
(9,10-Dimethoxy-5,8,13,13a-tetrahydro-6H-benzo[g]-1,3-benzodioxolo[5,6-a]quinolizin-13-yl)-propionic acid (13-carboxyethyl-tetrahydro berberine).

COMPARATIVE EXAMPLE

13-Benzyl-9,10-dimethoxy-5,6-dihydrobenzo[g]-1,3-benzodioxolo[5,6-a]quinolizinium iodide (13-Benzylberberine iodide)

The title compound was obtained by reacting 8-acetonyl-tetrahydroberberine with benzylbromide as described in Example 1 of U.S. Pat. No. 6,008,356 and U.S. Pat. No. 6,030,978.
NMR (200 MHz, CDCl$_3$): δ 10.60 (s, 1H), 7.70 (d, 1H), 7.60 (d, 1H), 7.40-7.20 (m, 3H), 7.11 (brd, 2H), 6.85 (s, 1H), 6.95 (s,1H), 6.00 (s, 2H), 5.35-5.20 (m, 2H), 4.68 (s, 2H), 4.38 (s, 3H), 4.00 (s, 2H), 3.25 (t, 2H).
Preparation of 13-substituted Tetrahydroprotoberberines of the General Formula (II-i)

EXAMPLE 1

13-[2-(Phenyl)ethyl]-9,10-dimethoxy-5,8,13,13a-tetrahydro-6H-benzo[g]-1,3-benzodioxolo[5,6-a]quinolizine

[13-(2-Phenyl)ethyl-tetrahydroberberine]

To a solution of dihydroberberine (338 mg, 1 mmol) and 2-phenylethylbromide (2.22 g, 12 mmol) in acetonitrile (25 mL) was added sodium iodide (450 mg, 3 mmol) and the resulting mixture was stirred for 16 h at reflux temperature under nitrogen. Then, the mixture was concentrated under vacuum, diluted with water and the unstable iminium salt filtered off and dried.
To a solution of the above obtained iminium salt in absolute ethanol, sodium borohydride (378 mg, 10 mmol) was added portionwise and the resulting suspension stirred for 45 min at room temperature. More sodium borohydride (302 mg, 8 mmol) was added and the suspension stirred for an additional hour at room temperature. The solvent was evaporated under vacuum, water was added and the mixture extracted with ethyl acetate. The combined organic phases were dried and then evaporated. The residue was chromatographed on silica gel eluting with hexane/ethyl acetate (10-20%) to give the title compound.
NMR (300 MHz, DMSO-d$_6$): δ 10.55 (s, 1H), 7.65 (d, 1H), 7.55 (d, 1H), 7.20 (m, 3H), 7.10 (brd, 2H), 6.90 (s, 1H), 6.80 (s,1H), 6.05 (s, 2H), 5.25 (m, 2H), 4.65 (m, 4H), 4.40 (s, 3H), 4.10 (s, 3H), 3.20 (t, 2H).
By proceeding analogously and starting from the appropriate haloalkyl(hetero)aryl compounds of the general formula (IVa, Z is a bond) or haloalkylene(hetero)aryl compounds of the general formula (IVb, Y is CH), the following compounds were obtained:
13-[2-(4-chlorophenyl)ethyl]-9,10-dimethoxy-5,8,13,13a-tetrahydro-6H-benzo[g]-1,3-benzodioxolo[5,6-a]quinolizine;
13-[2-(4-methoxyphenyl)ethyl]-9,10-dimethoxy-5,8,13,13a-tetrahydro-6H-benzo[g]-1,3-benzodioxolo[5,6-a]quinolizine;
13-[2-(4-methylphenyl)ethyl]-9,10-dimethoxy-5,8,13,13a-tetrahydro-6H-benzo[g]-1,3-benzodioxolo[5,6-a]quinolizine;
13-[2-(4-fluorophenyl)ethyl]-9,10-dimethoxy-5,8,13,13a-tetrahydro-6H-benzo[g]-1,3-benzodioxolo[5,6-a]quinolizine;
13-[2-(4-bromophenyl)ethyl]-9,10-dimethoxy-5,8,13,13a-tetrahydro-6H-benzo[g]-3-benzodioxolo[5,6-a]quinolizine;
13-[2-(4-trifluoromethylphenyl)ethyl]-9,10-dimethoxy-5,8,13,13a-tetrahydro-6H-benzo[g]-1,3-benzodioxolo[5,6-a]quinolizine;
13-[2-(4-trifluoromethoxyphenyl)ethyl]-9,10-dimethoxy-5,8,13,13a-tetrahydro-6H-benzo[g]-1,3-benzodioxolo[5,6-a]q quinolizine;
13-[2-(4-nitrophenyl)ethyl]-9,10-dimethoxy-5,8,13,13a-tetrahydro-6H-benzo[g]-1,3-benzodioxolo[5,6-a]quinolizine;
13-[2-(4-dimethylaminophenyl)ethyl]-9,10-dimethoxy-5,8,13,13a-tetrahydro-6H-benzo[g]-1,3-benzodioxolo[5,6-a]quinolizine;
13-[2-(4-acetylaminophenyl)ethyl]-9,10-dimethoxy-5,8,13,13a-tetrahydro-6H-benzo[g]-1,3-benzodioxolo[5,6-a]quinolizine;
13-[2-(4-ethoxycarbonylphenyl)ethyl]-9,10-dimethoxy-5,8,13,13a-tetrahydro-6H-benzo[g]-1,3-benzodioxolo[5,6-a]quinolizine;
13-[2-(naphth-1-yl)ethyl]-9,10-dimethoxy-5,8,13,13a-tetrahydro-6H-benzo[g]-1,3-benzodioxolo[5,6-a]quinolizine;
13-[2-(4-chloronaphth-1-yl)ethyl]-9,10-dimethoxy-5,8,13,13a-tetrahydro-6H-benzo[g]-1,3-benzodioxolo[5,6-a]quinolizine;
13-[2-(4-methoxynaphth-1-yl)ethyl]-9,10-dimethoxy-5,8,13,13a-tetrahydro-6H-benzo[g]-1,3-benzodioxolo[5,6-a]quinolizine;

13-[2-(4-nitronaphth-1-yl)ethyl]-9,10-dimethoxy-5,8,13,13a-tetrahydro-6H-benzo[g]-1,3-benzodioxolo[5,6-a]quinolizine;

13-[2-(4-ethoxycarbonylnaphth-1-yl)ethyl]-9,10-dimethoxy-5,8,13,13a-tetrahydro-6H-benzo[g]-1,3-benzodioxolo[5,6-a]quinolizine;

13-[2-(indol-3-yl)ethyl]-9,10-dimethoxy-5,8,13,13a-tetrahydro-6H-benzo[g]-1,3-benzodioxolo[5,6-a]quinolizine;

13-[2-(5-chloroindol-3-yl)ethyl)]-9,10-dimethoxy-5,8,13,13a-tetrahydro-6H-benzo[g]-1,3-benzodioxolo[5,6-a]quinolizine;

13-[2-(5-nitroindol-3-yl)ethyl]-9,10-dimethoxy-5,8,13,13a-tetrahydro-6H-benzo[g]-1,3-benzodioxolo[5,6-a]quinolizine;

13-[2-(5-methoxyindol-3-yl)ethyl]-9,10-dimethoxy-5,8,13,13a-tetrahydro-6H-benzo[g]-1,3-benzodioxolo[5,6-a]quinolizine;

13-[2-(5-ethoxycarbonylindol-3-yl)ethyl]-9,10-dimethoxy-5,8,13,13a-tetrahydro-6H-benzo[g]-1,3-benzodioxolo[5,6-a]quinolizine;

13-[3-(phenyl)propyl]-9,10-dimethoxy-5,8,13,13a-tetrahydro-6H-benzo[g]-1,3-benzodioxolo[5,6-a]quinolizine;

13-[3-(4-chlorophenyl)propyl]-9,10-dimethoxy-5,8,13,13a-tetrahydro-6H-benzo[g]-1,3-benzodioxolo[5,6-a]quinolizinium iodide;

13-[3-(4-fluorophenyl)propyl]-9,10-dimethoxy-5,8,13,13a-tetrahydro-6H-benzo[g]-1,3-benzodioxolo[5,6-a]quinolizine;

13-[3-(4-bromophenyl)propyl]-9,10-dimethoxy-5,8,13,13a-tetrahydro-6H-benzo[g]-1,3-benzodioxolo[5,6-a]quinolizine;

13-[3-(4-methylphenyl)propyl]-9,10-dimethoxy-5,8,13,13a-tetrahydro-6H-benzo[g]-1,3-benzodioxolo[5,6-a]quinolizine;

13-[3-(4-methoxyphenyl)propyl]-9,10-dimethoxy-5,8,13,13a-tetrahydro-6H-benzo[g]-1,3-benzodioxolo[5,6-a]quinolizine;

13-[3-(4-trifluoromethoxyphenyl)propyl]-9,10-dimethoxy-5,8,13,13a-tetrahydro-6H-benzo[g]-1,3-benzodioxolo[5,6-a]quinolizine;

13-[3-(4-trifluoromethylphenyl)propyl]-9,10-dimethoxy-5,8,13,13a-tetrahydro-6H-benzo[g]-1,3-benzodioxolo[5,6-a]quinolizine;

13-[3-(4-nitrophenyl)propyl]-9,10-dimethoxy-5,8,13,13a-tetrahydro-6H-benzo[g]-1,3-benzodioxolo[5,6-a]quinolizine;

13-[3-(4-dimethylaminophenyl)propyl]-9,10-dimethoxy-5,8,13,13a-tetrahydro-6H-benzo[g]-1,3-benzodioxolo[5,6-a]quinolizine;

13-[3-(4-acetamidophenyl)propyl]-9,10-dimethoxy-5,8,13,13a-tetrahydro-6H-benzo[g]-1,3-benzodioxolo[5,6-a]quinolizine;

13-[3-(4-ethoxycarbonylphenyl)propyl]-9,10-dimethoxy-5,8,13,13a-tetrahydro-6H-benzo[g]-1,3-benzodioxolo[5,6-a]quinolizine;

13-[3-(4-phenoxyphenyl)propyl]-9,10-dimethoxy-5,8,13,13a-tetrahydro-6H-benzo[g]-1,3-benzodioxolo[5,6-a]quinolizine;

13-[3-(naphth-1-yl)propyl]-9,10-dimethoxy-5,8,13,13a-tetrahydro-6H-benzo[g]-1,3-benzodioxolo[5,6-a]quinolizine;

13-[3-(4-chloronahth-1-yl)propyl]-9,10-dimethoxy-5,8,13,13a-tetrahydro-6H-benzo[g]-1,3-benzodioxolo[5,6-a]quinolizine;

13-[3-(4-methoxynaphth-1-yl)propyl]-9,10-dimethoxy-5,8,13,13a-tetrahydro-6H-benzo[g]-1,3-benzodioxolo[5,6-a]quinolizine;

13-[3-(4-nitronaphth-1-yl)propyl]-9,10-dimethoxy-5,8,13,13a-tetrahydro-6H-benzo[g]-1,3-benzodioxolo[5,6-a]quinolizine;

13-[3-(4-carbethoxynaphth-1-yl)propyl]-9,10-dimethoxy-5,8,13,13a-tetrahydro-6H-benzo[g]-1,3-benzodioxolo[5,6-a]quinolizine;

13-(3-indolylpropyl)-9,10-dimethoxy-5,8,13,13a-tetrahydro-6H-benzo[g]-1,3-benzodioxolo[5,6-a]quinolizine;

13-[3-(5-chloroindol-3-yl)propyl]-9,10-dimethoxy-5,8,13,13a-tetrahydro-6H-benzo[g]-1,3-benzodioxolo[5,6-a]quinolizine;

13-[3-(5-nitroindol-3-yl)propyl]-9,10-dimethoxy-5,8,13,13a-tetrahydro-6H-benzo[g]-1,3-benzodioxolo[5,6-a]quinolizine;

13-[3-(5-methoxyindol-3-yl)propyl]-9,10-dimethoxy-5,8,13,13a-tetrahydro-6H-benzo[g]-1,3-benzodioxolo[5,6-a]quinolizine;

13-[3-(5-carbethoxyindol-3-yl)propyl]-9,10-dimethoxy-5,8,13,13a-tetrahydro-6H-benzo[g]-1,3-benzodioxolo[5,6-a]quinolizine;

13-[(1,4-benzodioxan-2-yl)methyl]-9,10-dimethoxy-5,8,13,13a-tetrahydro-6H-benzo[g]-1,3-benzodioxolo[5,6-a]quinolizine;

13-[2,2'-bis(phenyl)ethyl)-9,10-dimethoxy-5,8,13,13a-tetrahydro-6H-benzo[g]-1,3-benzodioxolo[5,6-a]quinolizine;

13-[2,2-bis(4-chlorophenyl)ethyl]-9,10-dimethoxy-5,8,13,13a-tetrahydro-6H-benzo[g]-1,3-benzodioxolo[5,6-a]quinolizine;

13-[2,2-bis(4-bromophenyl)ethyl]-9,10-dimethoxy-5,8,13,13a-tetrahydro-6H-benzo[g]-1,3-benzodioxolo[5,6-a]quinolizine;

13-[2,2-bis(4-fluorophenyl)ethyl]-9,10-dimethoxy-5,8,13,13a-tetrahydro-6H-benzo[g]-1,3-benzodioxolo[5,6-a]quinolizine;

13-[2,2-bis(4-methylphenyl)ethyl]-9,10-dimethoxy-5,8,13,13a-tetrahydro-6H-benzo[g]-1,3-benzodioxolo[5,6-a]quinolizinium iodide;

13-[2,2-bis(4-methoxyphenyl)ethyl]-9,10-dimethoxy-5,8,13,13a-tetrahydro-6H-benzo[g]-1,3-benzodioxolo[5,6-a]quinolizine;

13-[3,3-bis(phenyl)propyl]-9,10-dimethoxy-5,8,13,13a-tetrahydro-6H-benzo[g]-1,3-benzodioxolo[5,6-a]quinolizine;

13-[3,3-bis(4-methylphenyl)propyl]-9,10-dimethoxy-5,8,13,13a-tetrahydro-6H-benzo[g]-1,3-benzodioxolo[5,6-a]quinolizine;

13-[3,3-bis(4-methoxyphenyl)propyl]-9,10-dimethoxy-5,8,13,13a-tetrahydro-6H-benzo[g]-1,3-benzodioxolo[5,6-a]quinolizine;

13-[3,3-bis(4-fluorophenyl)propyl]-9,10-dimethoxy-5,8,13,13a-tetrahydro-6H-benzo[g]-1,3-benzodioxolo[5,6-a]quinolizine;

13-[3,3-bis(4-chlorophenyl)propyl]-9,10-dimethoxy-5,8,13,13a-tetrahydro-6H-benzo[g]-1,3-benzodioxolo[5,6-a]quinolizine;

13-[3,3-bis(4-bromophenyl)propyl]-9,10-dimethoxy-5,8,13,13a-tetrahydro-6H-benzo[g]-1,3-benzodioxolo[5,6-a]quinolizine.

EXAMPLE 2

13-(Benzyloxy)methyl]-9,10-dimethoxy-5,8,13,13a-tetrahydro-6H-benzo[g]-1,3-benzodioxolo[5,6-a]quinolizine

[13-(Benzyloxy)methyl-tetrahydroberberine]

Dihydroberberine (338 mg, 1 mmol) and benzyl chloromethyl ether (3.44 mg, 15,5 mmol) were dissolved in acetonitrile (25 mL) and then sodium iodide (450 mg, 3 mmol) was added. The resulting suspension was stirred overnight at reflux. The cooled reaction mixture was concentrated under vacuum, diluted with water, the precipitated unstable iminium salt filtered off and dried.

To a solution of the iminium salt in absolute ethanol (25 mL) sodium borohydride (378 mg, 10 mmol) was added and the resulting mixture stirred for 30 min at room temperature. Then, more sodium borohydride (302 mg, 8 mmol) was added and the mixture stirred for another hour at room temperature. The solvent was evaporated under reduced pressure, water was added and the mixture extracted with ethyl acetate. The combined organic phases were dried and evaporated. The residue was chromatographed on silica gel using hexane/ethyl acetate (10-20%) as eluant to give the title compound.

NMR (300 MHz, DMSO-$d_6$): δ 9.50 (s, 1H), 7.90 (d, 1H), 7.85 (d, 1H), 7.05-7.60 (m, 5H), 5.80 (s, 2H), 7.4 (s, 1H), 7.35 (s, 1H), 4.80 (m, 2H), 3.9 (s, 3H), 3.85 (s, 3H), 3.2-3.3 (s, 4H)

By proceeding analogously and starting from the appropriate haloalkyloxyalkyl(hetero)aryl compounds of the general formula (IVa, Z is O(CH$_2$)$_m$, m≧1) or haloalkylene(hetero)aryl compounds of the general formula (IVb, Y is O(CH$_2$)$_m$—CH, m≧0), the following compounds were obtained:
13-[2-(benzyloxy)ethyl]-9,10-dimethoxy-5,8,13,13a-tetrahydro-6H-benzo[g]-1,3-benzodioxolo[5,6-a]quinolizine;
13-[(1,4-benzodioxan-2-yl)methyl]-9,10-dimethoxy-5,8,13,13a-tetrahydro-6H-benzo[g]-1,3-benzodioxolo[5,6-a]quinolizine;
13-[(4-chlorobenzyloxy)methyl]-9,10-dimethoxy-5,8,13,13a-tetrahydro-6H-benzo[g]-1,3-benzodioxolo[5,6-a]quinolizine;
13-[(4-methoxybenzyloxy)methyl]-9,10-dimethoxy-5,8,13,13a-tetrahydro-6H-benzo[g]-1,3-benzodioxolo[5,6-a]quinolizine;
13-[(4-dimethylaminobenzyloxy)methyl]-9,10-dimethoxy-5,8,13,13a-tetrahydro-6H-benzo[g]-1,3-benzodioxolo[5,6-a]quinolizine;
13-[(4-hydroxybenzyloxy)methyl]-9,10-dimethoxy-5,8,13,13a-tetrahydro-6H-benzo[g]-1,3-benzodioxolo[5,6-a]quinolizine.

EXAMPLE 3

13-[2-(Phenoxy)ethyl]-9,10-dimethoxy-5,8,13,13a-tetrahydro-6H-benzo[g]-1,3-benzodioxolo[5,6-a]quinolizine

[13-(2-Phenoxy)ethyltetrahydroberberine]

To a solution of dihydroberberine (338 mg, 1 mmol) and 2-phenoxyethylbromide (2.412 g, 12 mmol) in acetonitrile (25 mL) was added sodium iodide (900 mg, 6 mmol) and the resulting mixture was stirred overnight at reflux temperature under a nitrogen atmosphere. Thereafter the mixture was concentrated under vacuum, diluted with water and the unstable iminium salt filtered off and dried.

The iminium salt was dissolved in absolute ethanol (20 mL), then sodium borohydride (378 mg, 10 mmol) was added and the resulting suspension stirred for 30 min at room temperature. More sodium borohydride (378 mg, 10 mmol) was added and the mixture stirred for further 1 h at room temperature. The solvent was evaporated under vacuum, then water (60 mL) was added and the mixture extracted with ethyl acetate (3×100 mL). The combined organic phases were dried and evaporated to dryness. The residue was submitted to column chromatography using hexane-ethyl acetate (10-25%) as eluant to obtain the title compound.

NMR (200 MHz, DMSO-$d_6$) δ: 9.9 (s, 1H), 8.3 (d, 1H), 8.2 (d, 1H), 7.6 (d, 1H), 7.5 (d, 1H), 7.1-7.3 (m, 3H), 6.8 (m, 2H), 4.1 (s, 3H), 4.1 (s, 3H), 4.3 (m, 2H), 4.9 (m, 2H), 6.1 (s, 2H), 5.6 (m, 2H), 3.1 (t, 2H).

By proceeding analogously and starting from the appropriate haloalkyloxy(hetero)aryl compounds of the general formula (IVa, Z is O(CH$_2$)$_m$, m=0), the following compounds were obtained:
13-[3-(phenoxy)propyl]-9,10-dimethoxy-5,8,13,13a-tetrahydro-6H-benzo[g]-1,3-benzodioxolo[5,6-a]quinolizine;
13-[2-(p-chlorophenoxy)ethyl]-9,10-dimethoxy-5,8,13,13a-tetrahydro-6H-benzo[g]-1,3-benzodioxolo[5,6-a]quinolizine;
13-[2-(p-methoxyphenoxy)ethyl]-9,10-dimethoxy-5,8,13,13a-tetrahydro-6H-benzo[g]-1,3-benzodioxolo[5,6-a]quinolizinium iodide;
13-[2-(p-hydroxyphenoxy)ethyl]-9,10-dimethoxy-5,8,13,13a-tetrahydro-6H-benzo[g]-1,3-benzodioxolo[5,6-a]quinolizine;
13-[3-(p-chlorophenoxy)propyl]-9,10-dimethoxy-5,8,13,13a-tetrahydro-6H-benzo[g]-1,3-benzodioxolo[5,6-a]quinolizine;
13-[3-(p-methoxyphenoxy)propyl]-9,10-dimethoxy-5,8,13,13a-tetrahydro-6H-benzo[g]-1,3-benzodioxolo[5,6-a]quinolizine;
13-[3-(p-hydroxyphenoxy)propyl]-9,10-dimethoxy-5,8,13,13a-tetrahydro-6H-benzo[g]-1,3-benzodioxolo[5,6-a]quinolizine.

Preparation of 13-Substituted Tetrahydroprotoberberines of the General Formula (II-ii)

EXAMPLE 4

13-Benzylaminocarbonylmethyl-9,10-dimethoxy-5,8,13,13a-tetrahydro-6H-benzo[g]-1,3-benzodioxolo[5,6-a]quinolizine

[13-Benzylaminocarbonylmethyl-tetrahydroberberine]

A solution of the 13-acetic acid tetrahydroberberine of Preparative Example 4 (334 mg, 0.84 mmol) and benzylamine (180 mg, 1.68 mmol) in DMF (10 mL) was treated with 1-(3-dimethylaminopropyl)-3-ethyl carbodiimide hydrochloride (322 mg, 1.68 mmol) and dimethylaminopyridine (256 mg, 2.1 mmol) and the resulting solution was stirred for 24 h at room temperature. The reaction mixture was poured into ethyl acetate, and the organic phase washed with 10% HCl solution (2×50 ml) and saturated NaHCO$_3$ solution (2×20 ml). The organic phase was dried, concentrated and the residue chromatographed on a silica gel column eluting with hexane:ethyl acetate 8:2 to give the title compound in 75% yield (306 mg).

NMR (200 MHz, DMSO-d$_6$) δ: 8.1 (m, 1H), 7.2 (m, 3H), 7.1 (m, 2H), 6.8 (d, 1H), 6.7 (s,d,1H), 6.65 (m, 1H), 5.95 (s, 2H), 4.30 (m, 2H), 4.10 (m, 2H), 3.7 (s, 6H), 3.65 (m, 2H), 2.5 (d, 2H), 2.4 (d,2H).

By proceeding analogously and starting from the appropriate 13-alkanoic acid tetrahydroprotoberberines of the general formula (IX) and the appropriate amine derivatives of the general formulae (X), (XI), and (XII), the following compounds were obtained:

13-phenylaminocarbonylethyl-9,10-dimethoxy-5,8,13,13a-tetrahydro-6H-benzo[g]-1,3-benzodioxolo[5,6-a]quinolizine; NMR (200 MHz, DMSO-d$_6$): δ 9.6 (s, 1H), 7.5 (d, 2H), 7.25 (d, d, 3H), 7.0 (d, 2H), 6.9 (d, 1H), 6.8 (s, 1H), 6.8 (s, 1H), 6.6 (m, 1H), 4.1 (d, 2H), 3.8 (s, 6H), 3.7 (m, 2H), 2.5 (d, 2H), 2.4 (d, 2H);

13-[(4-pyridyl)aminocarbonylmethyl]-9,10-dimethoxy-5,8,13,13a-tetrahydro-6H-benzo[g]-1,3-benzodioxolo[5,6-a]quinolizine; NMR (200 MHz, DMSO-d$_6$): δ 10.0 (s, 1H), 8.4 (d, 2H), 7.5 (d, 2H), 7.0 (m, 4H), 6.7 (m, 1H), 6.0 (s, 1H), 5.9 (s, 1H), 4.15 (d, 2H), 3.9 (s, 6H), 3.8 (m, 2H), 2.6 (d, 2H), 2.5 (d, 2H);

13-[(1-indolyl)carbonylmethyl]-9,10-dimethoxy-5,8,13,13a-tetrahydro-6H-benzo[g]-1,3-benzodioxolo[5,6-a]quinolizine;

13-[(p-chlorobenzyl)aminocarbonylmethyl]-9,10-dimethoxy-5,8,13,13a-tetrahydro-6H-benzo[g]-1,3-benzodioxolo[5,6-a]quinolizine;

13-[(p-methoxybenzyl)aminocarbonylmethyl]-9,10-dimethoxy-5,8,13,13a-tetrahydro-6H-benzo[g]-1,3-benzodioxolo[5,6-a]quinolizine;

13-[(p-dimethylaminobenzyl)aminocarbonylmethyl]-9,10-dimethoxy-5,8,13,13a-tetrahydro-6H-benzo[g]-1,3-benzodioxolo[5,6-a]quinolizine;

13-[(p-hydroxybenzyl)aminocarbonymethyl]-9,10-dimethoxy-5,8,13,13a-tetrahydro-6H-benzo[g]-1,3-benzodioxolo[5,6-a]quinolizine;

13-[(p-chlorophenyl)aminocarbonylmethyl]-9,10-dimethoxy-5,8,13,13a-tetrahydro-6H-benzo[g]-1,3-benzodioxolo[5,6-a]quinolizine;

13-[(p-methoxyphenyl)aminocarbonylmethyl]-9,10-dimethoxy-5,8,13,13a-tetrahydro-6H-obenzo[g]-1,3-benzodioxolo[5,6-a]quinolizine;

13-[(p-dimethylaminophenyl)aminocarbonylmethyl]-9,10-dimethoxy-5,8,13,13a-tetrahydro-6H-benzo[g]-1,3-benzodioxolo[5,6-a]quinolizine;

13-[(p-hydroxyphenyl)aminocarbonylmethyl]-9,10-dimethoxy-5,8,13,13a-tetrahydro6H-benzo[g]-1,3-benzodioxolo[5,6-a]quinolizine;

13-[(5-chloroindol-1-yl)carbonylmethyl]-9,10-dimethoxy-5,8,13,13a-tetrahydro-6H-benzo[g]-1,3-benzodioxolo[5,6-a]quinolizine;

13-[(5-methoxyindol-1-yl)carbonylmethyl]-9,10-dimethoxy-5,8,13,13a-tetrahydro-6H-benzo[g]-1,3-benzodioxolo[5,6-a]quinolizine;

13-[(5-hydroxyindol-1-yl)carbonylmethyl]-9,10-dimethoxy-5,8,13,13a-tetrahydro-6H-benzo[g]-1,3-benzodioxolo[5,6-a]quinolizine;

13-[(5-dimethylaminoindol-1-yl)carbonylmethyl]-9,10-dimethoxy-5,8,13,13a-tetrahydro-6H-benzo[g]-1,3-benzodioxolo[5,6-a]quinolizine.

Preparation of 13-Substituted Tetrahydroprotoberberines of the General Formula (II-iii)

EXAMPLE 5

13-Benzylcarbonylaminomethyl-9,10-dimethoxy-5,8,13,13a-tetrahydro-6H-benzo[g]-1,3-benzodioxolo[5,6-a]quinolizine (13-Benzylcarbonylaminomethyl-tetrahydroberberine)

Triethylamine (1.02 g, 1.02 mmol) and diphenylphosphorylazide (2.75 g, 10 mmol) were added under stirring at room temperature to a suspension of 13-(carboxymethyl)-tetrahydroberberine (3.972 g, 10 mmol) in acetonitrile (30 mL). After 2 h additional stirring at room temperature the mixture was partitioned between chloroform and 5% aqueous sodium bicarbonate. The combined organic phases were dried and evaporated to give 13-(azidocarbonylmethyl)-tetrahydroberberine (3.80 g, 90% yield).

A stirred suspension of the 13-(azidocarbonylmethyl)-tetrahydroberberine (3.80 g, 9 mmol) so obtained, phenylacetic acid (1.226 g, 9 mmol), and triethylamine (0.911 g, 9 mmol) in benzene was heated at reflux in a nitrogen atmosphere for about 8 h. The reaction mixture was cooled, the precipitate filtered, washed with small portions of benzene and then chromatographed on a silica gel column using hexane—ethyl acetate 8:2 as eluant to give the title compound (3.063 g, 70% yield).

NMR (200 MHz, DMSO-d$_6$) δ: 8.2 (m,1H), 7.3 (m, 3H), 7.2 (m, 2H), 6.9 (d, 1H), 6,8 (d, 1H), 6.7 (s, 2H), 6.6 (m, 1H), 6.0 (s, 2H), 4.3 (m, 2H), 4.2 (m, 2H), 3,7 (s, 6H), 3.65 (m, 2H), 2.55 (m, 2H), 2.5 (d, 2H).

By proceeding analogously and starting from the appropriate 13-alkanoic acid tetrahydroprotoberberines of the general formula (IX) and the appropriate acid derivatives of the general formulae (XIV), (XV), and (XVI), the following compounds were obtained:

13-phenylcarbonylaminomethyl-9,10-dimethoxy-5,8,13,13a-tetrahydro-6H-benzo[g]-1,3-benzodioxolo[5,6-a]quinolizine;

13-[(4-pyridyl)carbonylaminomethyl]-9,10-dimethoxy-5,8,13,13a-tetrahydro-6H-benzo[g]-1,3-benzodioxolo[5,6-a]quinolizine;

13-[(p-chlorobenzyl)carbonylaminomethyl]-9,10-dimethoxy-5,8,13,13a-tetrahydro-6H-benzo[g]-1,3-benzodioxolo[5,6-a]quinolizine;

13-[(p-methoxybenzyl)carbonylaminomethyl]-9,10-dimethoxy-5,8,13,13a-tetrahydro-6H-benzo[g]-1,3-benzodioxolo[5,6-a]quinolizine;

13-[(p-hydroxybenzyl)carbonylaminomethyl]-9,10-dimethoxy-5,8,13,13a-tetrahydro-6H-benzo[g]-1,3-benzodioxolo[5,6-a]quinolizine;

13-[(p-chlorophenyl)carbonylaminomethyl]-9,10-dimethoxy-5,8,13,13a-tetrahydro-6H-benzo[g]-1,3-benzodioxolo[5,6-a]quinolizine;

13-[(p-methoxyphenyl)carbonylaminomethyl]-9,10-dimethoxy-5,8,13,13a-tetrahydro-6H-benzo[g]-1,3-benzodioxolo[5,6-a]quinolizine;

13-[(p-hydroxyphenyl)carbonylaminomethyl]-9,10-dimethoxy-5,8,13,13a-tetrahydro-6H-benzo[g]-1,3-benzodioxolo[5,6-a]quinolizine.

Preparation of the Compounds of the Invention

EXAMPLE 6

13-[2-(Phenyl)ethyl]-9,10-dimethoxy-5,6-dihydrobenzo[g]-1,3-benzodioxolo [5,6-a]quinolizinium iodide

[13-(2-Phenyl)ethylberberine iodide]

To a solution of 13-[(2-(phenyl)ethyl]-tetrahydroberberine (1 mmol, 445 mg) in absolute ethanol (30 mL) was added iodine (762 mg, 3 mmol) and the mixture refluxed for 6 h. More iodine (1.5 mmol, 381 mg) was then added and the mixture refluxed for further 10 h. The excess iodine was decomposed by addition of sodium thiosulfate until the brown solution changed to yellow colour and a yellow precipitate was formed. The solid was filtered off and the filtrate evaporated to dryness. The residue was chromatographed on a silica gel column eluting with 1-3% methanol in dichloromethane to give 512 mg of title compound (90% yield).

NMR (200 MHz, DMSO-$d_6$) δ: 10.5 (s, 1H), 7.7 (d, 1H), 7.6 (d, 1H), 7.2 (m, 3H), 7.1 (d, 3H), 6.9 (s, 1H), 6.8 (s, 1H), 6.0 (s, 2H), 5.2 (m, 2H), (4.7 (m, 4H), 4.3 (s, 3H), 4.1 (s, 3H), 3.2 (t, 2H).

By proceeding analogously and starting from the appropriate 13-substituted tetrahydroprotoberberines as prepared as described in the above Examples 1-5, the following compounds of the invention were obtained:

13-[2-(4-chlorophenyl)ethyl]-9,10-dimethoxy-5,6-dihydrobenzo[g]-1,3-benzodioxolo[5,6-a]quinolizinium iodide; NMR (200 MHz, DMSO-$d_6$) δ: 10.02 (s,1H), 9.87 (s, 1H), 9.86 (s,1H), 8.33 (d, 1H), 8.24 (d, 1H), 7.95 (d, 1H), 7.38 (d, 2H), 7.22 (d,2H), 7.05 (s, 2H), 6.16 (s, 2H), 4.12 (s, 3H), 4.11 (s,3H), 4.02 (m, 2H), 3.29 (t, 2H), 2.88 (m, 4H);

13-[2-(4-methoxyphenyl)ethyl]-9,10-dimethoxy-5,6-dihydrobenzo[g]-1,3-benzodioxolo[5,6-a]quinolizinium iodide; NMR (200 MHz, DMSO-$d_6$) δ: 9.86 (s, 1H), 8.32 (d, 1H), 7.85 (d,1H), 7.40 (s,1H), 7.07 (s, 1H), 6.76 (m, 4H), 6.54 (d, 1H), 6.17 (s, 2H), 6.04 (t, 1H), 4.73 (m, 2H), 4.12 (s, 3H), 3.70 (s, 3H), 3.28 (t, 2H), 2.89 (m, 4H);

13-[2-(4-methylphenyl)ethyl]-9,10-dimethoxy-5,6-dihydrobenzo[g]-1,3-benzodioxolo[5,6-a]quinolizinium iodide;

13-[2-(4-fluorophenyl)ethyl]-9,10-dimethoxy-5,6-dihydrobenzo[g]-1,3-benzodioxolo[5,6-a]quinolizinium iodide;

13-[2-(4-bromophenyl)ethyl]-9,10-dimethoxy-5,6-dihydrobenzo[g]-1,3-benzodioxolo[5,6-a]quinolizinium iodide;

13-[2-(4-trifluoromethylphenyl)ethyl]-9,10-dimethoxy-5,6-dihydrobenzo[g]-1,3-benzodioxolo[5,6-a]quinolizinium iodide;

13-[2-(4-trifluoromethoxyphenyl)ethyl]-9,10-dimethoxy-5,6-dihydrobenzo[g]-1,3-benzodioxolo[5,6-a]quinolizinium iodide;

13-[2-(4-nitrophenyl)ethyl]-9,10-dimethoxy-5,6-dihydrobenzo[g]-1,3-benzodioxolo[5,6-a]quinolizinium iodide;

13-[2-(4-dimethylaminophenyl)ethyl]-9,10-dimethoxy-5,6-dihydrobenzo[g]-1,3-benzodioxolo[5,6-a]quinolizinium iodide;

13-[2-(4-acetylaminophenyl)ethyl]-9,10-dimethoxy-5,6-dihydrobenzo[g]-1,3-benzodioxolo[5,6-a]quinolizinium iodide;

13-[2-(4-ethoxycarbonylphenyl)ethyl]-9,10-dimethoxy-5,6-dihydrobenzo[g]-1,3-benzodioxolo[5,6-a]quinolizinium iodide;

13-[2-(naphth-1-yl)ethyl]-9,10-dimethoxy-5,6-dihydrobenzo[g]-1,3-benzodioxolo[5,6-a]quinolizinium iodide; NMR (200 MHz, DMSO-$d_6$) δ: 9.90 (s, 1H), 8.2 (m, 2H), 8.0 (m, 2H), 7.8 (d, 2H), 7.1 (d, 2H), 6.15 (s, 2H), 4.9 (m, 2H), 4.13 (s, 3H), 4.10 (s, 3H), 3.5 (s, 2H), 3.2 (m, 2H);

13-[2-(4-chloronaphth-1-yl)ethyl]-9,10-dimethoxy-5,6-dihydrobenzo[g]-1,3-benzodioxolo[5,6-a]quinolizinium iodide;

13-[2-(4-methoxynaphth-1-yl)ethyl]-9,10-dimethoxy-5,6-dihydrobenzo[g]-1,3-benzodioxolo[5,6-a]quinolizinium iodide;

13-[2-(4-nitronaphth-1-yl)ethyl]-9,10-dimethoxy-5,6-dihydrobenzo[g]-1,3-benzodioxolo[5,6-a]quinolizinium iodide;

13-[2-(4-ethoxycarbonylnaphth-1-yl)ethyl]-9,10-dimethoxy-5,6-dihydrobenzo[g]-1,3-benzodioxolo[5,6-a]quinolizinium iodide;

13-[2-(indol-3-yl)ethyl]-9,10-dimethoxy-5,6-dihydrobenzo[g]-1,3-benzodioxolo[5,6-a]quinolizinium iodide; NMR (200 MHz, DMSO-$d_6$) δ: 9.85 (s, 1H), 8.9 (s, 1H), 7.9-8.3 (m, 4H), 6.8-7.4 (m, 8H), 7.8 (d, 11H), 7.7 (d, 1H), 7.3 (s, 1H), 4.15 (s, 3H), 4.10 (s, 3H), 3.1 (d, 2H), 2.5-2.8 (m, 4H);

13-[2-(5-chloroindol-3-yl)ethyl)]-9,10-dimethoxy-5,6-dihydrobenzo[g]-1,3-benzodioxolo[5,6-a]quinolizinium iodide;

13-[2-(5-nitroindol-3-yl)ethyl]-9,10-dimethoxy-5,6-dihydrobenzo[g]-1,3-benzodioxolo[5,6-a]quinolizinium iodide;

13-[2-(5-methoxyindol-3-yl)ethyl]-9,10-dimethoxy-5,6-dihydrobenzo[g]-1,3-benzodioxolo[5,6-a]quinolizinium iodide;

13-[2-(5-ethoxycarbonylindol-3-yl)ethyl]-9,10-dimethoxy-5,6-dihydrobenzo[g]-1,3-benzodioxolo[5,6-a]quinolizinium iodide;

13-[3-(phenyl)propyl]-9,10-dimethoxy-5,6-dihydrobenzo[g]-1,3-benzodioxolo[5,6-a]quinolizinium iodide; NMR (200 MHz, DMSO-$d_6$) δ: 9.88 (s, 1H), 8.19 (d, 1H), 8.20 (d, 1H), 7.70 (m, 1H), 7.29 (s, 1H), 7.16 (s, 1H), 6.18 (s, 2H), 4.80 (m, 2H), 4.00 (s, 3H), 3.10 (t, 2H), 2.50 (m, 4H);

13-[3-(4-chlorophenyl)propyl]-9,10-dimethoxy-5,6-dihydrobenzo[g]-1,3-benzodioxolo[5,6-a]quinolizinium iodide;

13-[3-(4-fluorophenyl)propyl]-9,10-dimethoxy-5,6-dihydrobenzo[g]-1,3-benzodioxolo[5,6-a]quinolizinium iodide;

13-[3-(4-bromophenyl)propyl]-9,10-dimethoxy-5,6-dihydrobenzo[g]-1,3-benzodioxolo[5,6-a]quinolizinium iodide;

13-[3-(4-methylphenyl)propyl]-9,10-dimethoxy-5,6-dihydrobenzo[g]-1,3-benzodioxolo[5,6-a]quinolizinium iodide;

13-[3-(4-methoxyphenyl)propyl]-9,10-dimethoxy-5,6-dihydrobenzo[g]-1,3-benzodioxolo[5,6-a]quinolizinium iodide;

13-[3-(4-trifluoromethoxyphenyl)propyl]-9,10-dimethoxy-5,6-dihydrobenzo[g]-1,3-benzodioxolo[5,6-a]quinolizinium iodide;

13-[3-(4-trifluoromethylphenyl)propyl]-9,10-dimethoxy-5,6-dihydrobenzo[g]-1,3-benzodioxolo[5,6-a]quinolizinium iodide;

13-[3-(4-nitrophenyl)propyl]-9,10-dimethoxy-5,6-dihydrobenzo[g]-1,3-benzodioxolo[5,6-a]quinolizinium iodide;

13-[3-(4-dimethylaminophenyl)propyl]-9,10-dimethoxy-5,6-dihydrobenzo[g]-1,3-benzodioxolo[5,6-a]quinolizinium iodide;

13-[3-(4-acetamidophenyl)propyl]-9,10-dimethoxy-5,6-dihydrobenzo[g]-1,3-benzodioxolo[5,6-a]quinolizinium iodide;

13-[3-(4-ethoxycarbonylphenyl)propyl]-9,10-dimethoxy-5,6-dihydrobenzo[g]-1,3-benzodioxolo[5,6-a]quinolizinium iodide;

13-[3-(4-phenoxyphenyl)propyl]-9,10-dimethoxy-5,6-dihydrobenzo[g]-1,3-benzodioxolo[5,6-a]quinolizinium iodide;

13-[3-(naphth-1-yl)propyl]-9,10-dimethoxy-5,6-dihydrobenzo[g]-1,3-benzodioxolo[5,6-a]quinolizinium iodide;

13-[3-(4-chloronaphth-1-yl)propyl]-9,10-dimethoxy-5,6-dihydrobenzo[g]-1,3-benzodioxolo[5,6-a]quinolizinium iodide;

13-[3-(4-methoxynaphth-1-yl)propyl]-9,10-dimethoxy-5,6-dihydrobenzo[g]-1,3-benzodioxolo[5,6-a]quinolizinium iodide;

13-[3-(4-nitronaphth-1-yl)propyl]-9,10-dimethoxy-5,6-dihydrobenzo[g]-1,3-benzodioxolo[5,6-a]quinolizinium iodide;

13-[3-(4-carbethoxynaphth-1-yl)propyl]-9,10-dimethoxy-5,6-dihydrobenzo[g]-1,3-benzodioxolo[5,6-a]quinolizinium iodide;

13-(3-indolylpropyl)-9,10-dimethoxy-5,6-dihydrobenzo[g]-1,3-benzodioxolo[5,6-a]quinolizinium iodide;

13-[3-(5-chloroindol-3-yl)propyl]-9,10-dimethoxy-5,6-dihydrobenzo[g]-1,3-benzodioxolo[5,6-a]quinolizinium iodide;

13-[3-(5-nitroindol-3-yl)propyl]-9,10-dimethoxy-5,6-dihydrobenzo[g]-1,3-benzodioxolo[5,6-a]quinolizinium iodide;

13-[3-(5-methoxyindol-3-yl)propyl]-9,10-dimethoxy-5,6-dihydrobenzo[g]-1,3-benzodioxolo[5,6-a]quinolizinium iodide;

13-[3-(5-carbethoxyindol-3-yl)propyl]-9,10-dimethoxy-5,6-dihydrobenzo[g]-1,3-benzodioxolo[5,6-a]quinolizinium iodide;

13-[(1,4-benzodioxan-2-yl)methyl]-9,10-dimethoxy-5,6-dihydrobenzo[g]-1,3-benzodioxolo[5,6-a]quinolizinium chloride;

13-[2,2-bis(phenyl)ethyl)-9,10-dimethoxy-5,6-dihydrobenzo[g]-1,3-benzodioxolo[5,6-a]quinolizinium iodide;

13-[2,2-bis(4-chlorophenyl)ethyl]-9,10-dimethoxy-5,6-dihydrobenzo[g]-1,3-benzodioxolo[5,6-a]quinolizinium iodide;

13-[2,2-bis(4-bromophenyl)ethyl]-9,10-dimethoxy-5,6-dihydrobenzo[g]-1,3-benzodioxolo[5,6-a]quinolizinium iodide;

13-[2,2-bis(4-fluorophenyl)ethyl]-9,10-dimethoxy-5,6-dihydrobenzo[g]-1,3-benzodioxolo[5,6-a]quinolizinium iodide;

13-[2,2-bis(4-methylphenyl)ethyl]-9,10-dimethoxy-5,6-dihydrobenzo[g]-1,3-benzodioxolo[5,6-a]quinolizinium iodide;

13-[2,2-bis(4-methoxyphenyl)ethyl]-9,10-dimethoxy-5,6-dihydrobenzo[g]-1,3-benzodioxolo[5,6-a]quinolizinium iodide;

13-[3,3-bis(phenyl)propyl]-9,10-dimethoxy-5,6-dihydrobenzo[g]-1,3-benzodioxolo[5,6-a]quinolizinium iodide; NMR (200 MHz, DMSO-$d_6$) δ: 9.90 (s, 1H), 8.2 (d, 1H), 8.1 (d, 1H), 7.2 (m, 10H), 7.1 (s, 2H), 6.2 (s, 2H), 4.8 (m, 2H), 4.15 (s, 3H), 4.10 (s, 3H), 4.0 (d, 1H), 3.2 (t, 2H), 2.5 (m, propyl);

13-[3,3-bis(4-methylphenyl)propyl]-9,10-dimethoxy-5,6-dihydrobenzo[g]-1,3-benzodioxolo[5,6-a]quinolizinium iodide;

13-[3,3-bis(4-methoxyphenyl)propyl]-9,10-dimethoxy-5,6-dihydrobenzo[g]-1,3-benzodioxolo[5,6-a]quinolizinium iodide;

13-[3,3-bis(4-fluorophenyl)propyl]-9,10-dimethoxy-5,6-dihydrobenzo[g]-1,3-benzodioxolo[5,6-a]quinolizinium iodide;

13-[3,3-bis(4-chlorophenyl)propyl]-9,10-dimethoxy-5,6-dihydrobenzo[g]-1,3-benzodioxolo[5,6-a]quinolizinium iodide;

13-[3,3-bis(4-bromophenyl)propyl]-9,10-dimethoxy-5,6-dihydrobenzo[g]-1,3-benzodioxolo[5,6-a]quinolizinium iodide;

13-benzyloxymethyl-9,10-dimethoxy-5,6-dihydrobenzo[g]-1,3-benzodioxolo[5,6-a]quinolizinium iodide; NMR (200 MHz, DMSO-$d_6$) δ: 9.5 (s, 1H), 7.90 (d, 1H), 7.85 (d, 1H), 7.0-7.6 (m, 5H), 5.8 (s, 2H), 7.4 (s, 1H), 7.3 (s, 1H), 4.8 m, 2H), 3.8 (s, 3H), 3.9 (s, 3H), 3.2 (s, 4H);

13-[2-(phenoxy)ethyl]-9,10-dimethoxy-5,6-dihydrobenzo[g]-1,3-benzodioxolo[5,6-a]quinolizinium iodide;

13-[2-(benzyloxy)ethyl]-9,10-dimethoxy-5,6-dihydrobenzo[g]-1,3-benzodioxolo[5,6-a]quinolizinium iodide;

13-[3-(phenoxy)propyl]-9,10-dimethoxy-5,6-dihydrobenzo[g]-1,3-benzodioxolo[5,6-a]quinolizinium iodide;

13-[(1,4-benzodioxan-2-yl)methyl]-9,10-dimethoxy-5,6-dihydrobenzo[g]-1,3-benzodioxolo[5,6-a]quinolizinium iodide; NMR (200 MHz, DMSO-$d_6$) δ: 9.9 (s, 1H), 8.2 (d, 1H), 8.2 (d, 1H), 6.1 (s, 2H), 4.1 (s, 3H), 4.1 (s, 3H), 7.4 (s, 1H), 7.1 (s, 1H), 7.0-7.6 (m, 4H), 5.9-6.0 (m, 4H), 4.9 (m, 2H), 3.1 (t, 2H), 3.5 (d, 2H);

13-[(4-chlorobenzyloxy)methyl]-9,10-dimethoxy-5,6-dihydrobenzo[g]-1,3-benzodioxolo[5,6-a]quinolizinium iodide;

13-[(4-methoxybenzyloxy)methyl]-9,10-dimethoxy-5,6-dihydrobenzo[g]-1,3-benzodioxolo[5,6-a]quinolizinium iodide;

13-[(4-dimethylaminobenzyloxy)methyl]-9,10-dimethoxy-5,6-dihydrobenzo[g]-1,3-benzodioxolo[5,6-a]quinolizinium iodide;

13-[(4-hydroxybenzyloxy)methyl]-9,10-dimethoxy-5,6-dihydrobenzo[g]-1,3-benzodioxolo[5,6-a]quinolizinium iodide;

13-[2-(p-chlorophenoxy)ethyl]-9,10-dimethoxy-5,6-dihydrobenzo[g]-1,3-benzodioxolo[5,6-a]quinolizinium iodide;

13-[2-(p-methoxyphenoxy)ethyl]-9,10-dimethoxy-5,6-dihydrobenzo[g]-1,3-benzodioxolo[5,6-a]quinolizinium iodide;

13-[2-(p-hydroxyphenoxy)ethyl]-9,10-dimethoxy-5,6-dihydrobenzo[g]-1,3-benzodioxolo[5,6-a]quinolizinium iodide;

13-[2-(p-chlorobenzyloxy)ethyl]-9,10-dimethoxy-5,6-dihydrobenzo[g]-1,3-benzodioxolo[5,6-a]quinolizinium iodide;

13-[2-(p-methoxybenzyloxy)ethyl]-9,10-dimethoxy-5,6-dihydrobenzo[g]-1,3-benzodioxolo[5,6-a]quinolizinium iodide;

13-[2-(p-hydroxybenzyloxy)ethyl]-9,10-dimethoxy-5,6-dihydrobenzo[g]-1,3-benzodioxolo[5,6-a]quinolizinium iodide;

13-[3-(p-chlorophenoxy)propyl]-9,10-dimethoxy-5,6-dihydrobenzo[g]-1,3-benzodioxolo[5,6-a]quinolizinium iodide;

13-[3-(p-methoxyphenoxy)propyl]-9,10-dimethoxy-5,6-dihydrobenzo[g]-1,3-benzodioxolo[5,6-a]quinolizinium iodide;

13-[3-(p-hydroxyphenoxy)propyl]-9,10-dimethoxy-5,6-dihydrobenzo[g]-1,3-benzodioxolo[5,6-a]quinolizinium iodide;

13-[2-(diphenylmethyloxy)ethyl]-9,10-dimethoxy-5,6-dihydrobenzo[g]-1,3-benzodioxolo[5,6-a]quinolizinium iodide;

13-diphenylmethyloxymethyl-9,10-dimethoxy-5,6-dihydrobenzo[g]-1,3-benzodioxolo[5,6-a]quinolizinium iodide;

13-benzylaminocarbonylmethyl-9,10-dimethoxy-5,6-dihydrobenzo[g]-1,3-benzodioxolo[5,6-a]quinolizinium iodide; NMR (200 MHz, DMSO-$d_6$) δ:10.0 (s, 1H), 9.1 (m, 1H), 8.15 (d, 1H), 7.95 (d, 1H), 7.55-7.10 (m, 9H), 6.10 (s, 1H), 4.8 (m, 2H), 4.45 (d, 2H), 4.30 (d, 2H), 4.10 (s, 3H), 4.08 (s, 3H), 3.50 (d, 2H);

13-phenylaminocarbonylmethyl-9,10-dimethoxy-5,6-dihydrobenzo[g]-1,3-benzodioxolo[5,6-a]quinolizinium iodide; NMR (200 MHz, DMSO-$d_6$) δ: 10.7 (s, 1H), 10.0 (s, 1H), 8.2 (d, 1H), 8.1 (d, 1H), 7.7 (m, 3H), 7.5 (s, 2H), 7.35 (m, 2H), 7.2 (s, 1H), 7.1 (s, 1H), 6.1 (s, 2H), 4.85 (d, 2H), 4.5 (s, 2H), 4.1 (s, 2H), 4.1 (s, 2H), 3.20 (d, 2H);

13-[(4-pyridyl)aminocarbonylmethyl]-9,10-dimethoxy-5,6-dihydrobenzo[g]-1,3-benzodioxolo[5,6-a]quinolizinium iodide; NMR (200 MHz, DMSO-$d_6$) δ: 11.1 (s, 1H), 10.0 (s, 1H), 8.5 (d, 2H), 8.2 (d, 1H), 8.0 (d, 1H), 7.6 (m, 2H), 7.3 (s, 1H), 7.2 (s, 1H), 6.1 (s, 2H), 4.9 (m, 2H), 4.1 (s, 3H), 4.15 (s, 3H), 3.5 (s, 2H), 3.2 (s, 2H);

13-[(1-indolyl)carbonylmethyl)-9,10-dimethoxy-5,6-dihydrobenzo[g]-1,3-benzodioxolo[5,6-a]quinolizinium iodide;

13-[(p-chlorobenzyl)aminocarbonylmethyl]-9,10-dimethoxy-5,6-dihydrobenzo[g]-1,3-benzodioxolo[5,6-a]quinolizinium iodide;

13-[(p-methoxybenzyl)aminocarbonylmethyl]-9,10-dimethoxy-5,6-dihydrobenzo[g]-1,3-benzodioxolo[5,6-a]quinolizinium iodide;

13-[(p-dimethylaminobenzyl)aminocarbonylmethyl]-9,10-dimethoxy-5,6-dihydrobenzo[g]-1,3-benzodioxolo[5,6-a]quinolizinium iodide;

13-[(p-hydroxybenzyl)aminocarbonymethyl]-9,10-dimethoxy-5,6-dihydrobenzo[g]-1,3-benzodioxolo[5,6-a]quinolizinium iodide;

13-[(p-chlorophenyl)aminocarbonylmethyl]-9,10-dimethoxy-5,6-dihydrobenzo[g]-1,3-benzodioxolo[5,6-a]quinolizinium iodide;

13-[(p-methoxyphenyl)aminocarbonylmethyl]-9,10-dimethoxy-5,6-dihydrobenzo[g]-1,3-benzodioxolo[5,6-a]quinolizinium iodide;

13-[(p-dimethylaminophenyl)aminocarbonylmethyl]-9,10-dimethoxy-5,6-dihydrobenzo[g]-1,3-benzodioxolo[5,6-a]quinolizinium iodide;

13-[(p-hydroxyphenyl)aminocarbonylmethyl]-9,10-dimethoxy-5,6-dihydrobenzo[g]-1,3-benzodioxolo[5,6-a]quinolizinium iodide;

13-[(5-chloroindol-1-yl)carbonylmethyl]-9,10-dimethoxy-5,6-dihydrobenzo[g]-1,3-benzodioxolo[5,6-a]quinolizinium iodide; NMR (200 MHz, DMSO-$d_6$) δ: 10.0 (s, 1H), 7.9-8.3)m, 4H), 7.8 (d,1H), 7.7 (d, 1H), 7.4 (d, 1H), 7.2 (d, 1H), 6.9-7.1 (m, 1H), 6,1 (s, 1H), 6.2 (s, 1H), 5.3 (s, 2H), 4.9 (m, 2H), 4.15 (s, 3H), 4.10 (3H), 3.3 (m, 2H)

13-[(5-methoxyindol-1-yl)carbonylmethyl]-9,10-dimethoxy-5,6-dihydrobenzo[g]-1,3-benzodioxolo[5,6-a]quinolizinium iodide;

13-[(5-hydroxyindol-1-yl)carbonylmethyl]-9,10-dimethoxy-5,6-dihydrobenzo[g]-1,3-benzodioxolo[5,6-a]quinolizinium iodide;

13-[(5-dimethylaminoindol-1-yl)carbonylmethyl]-9,10-dimethoxy-5,6-dihydrobenzo[g]-1,3-benzodioxolo[5,6-a]quinolizinium iodide;

13-benzylcarbonylaminomethyl-9,10-dimethoxy-5,6-dihydrobenzo[g]-1,3-benzodioxolo[5,6-a]quinolizinium iodide;

13-phenylcarbonylaminomethyl-9,10-dimethoxy-5,6-dihydrobenzo[g]-1,3-benzodioxolo[5,6-a]quinolizinium iodide;

13-[(4-pyridyl)carbonylaminomethyl]-9,10-dimethoxy-5,6-dihydrobenzo[g]-1,3-benzodioxolo[5,6-a]quinolizinium iodide;

13-[(p-chlorobenzyl)carbonylaminomethyl]-9,10-dimethoxy-5,6-dihydrobenzo[g]-1,3-benzodioxolo[5,6-a]quinolizinium iodide;

13-[(p-methoxybenzyl)carbonylaminomethyl]-9,10-dimethoxy-5,6-dihydrobenzo[g]-1,3-benzodioxolo[5,6-a]quinolizinium iodide;

13-[(p-hydroxybenzyl)carbonylaminomethyl]-9,10-dimethoxy-5,6-dihydrobenzo[g]-1,3-benzodioxolo[5,6-a]quinolizinium iodide;

13-[(p-chlorophenyl)carbonylaminomethyl]-9,10-dimethoxy-5,6-dihydrobenzo[g]-1,3-benzodioxolo[5,6-a]quinolizinium iodide;

13-[(p-methoxyphenyl)carbonylaminomethyl]-9,10-dimethoxy-5,6-dihydrobenzo[g]-1,3-benzodioxolo[5,6-a]quinolizinium iodide; and 13-[(p-hydroxyphenyl)carbonylaminomethyl]-9,10-dimethoxy-5,6-dihydrobenzo[g]-1,3-benzodioxolo[5,6-a]quinolizinium iodide.

EXAMPLE 7

13-[2-(Phenoxy)ethyl]-9,10-dimethoxy-5,6-dihydrobenzo[g]-1,3-benzodioxolo[5,6-a]quinolizinium chloride

[13-(2-Phenoxy)ethylberberine chloride]

To a solution of 13-[2-(phenoxy)ethyl]-tetrahydroberberine (446 mg, 1 mmol) in chloroform (25 mL) was added N-chlorosuccinimide (320 mg, 2.4 mmol) and the mixture refluxed for 3 h. The organic phase was washed with water, dried and evaporated under vacuum. The residue was chromatographed on a silica gel column and eluting with DCM—MeOH 1-3% to give 287 mg of title compound (60% yield).

NMR (200 MHz, DMSO-$d_6$) δ: 9.9 (s, 1H), 8.3 (d, 1H), 8.2 (d, 1H), 7.6 (d, 1H), 7.5 (d, 1H), 7.1-7.3 (m, 3H), 6.8 (m, 2H), 6.1 (s, 2H), 5.6 (m, 2H ), 4.9 m, 2H), 4.3 (m, 2H), 4.1 (s, 3H), 4.05 (s, 3H), 3.1 (t, 2H)

EXAMPLE 8

13-[3-(phenyl)propyl]-9,10-dimethoxy-5,6-dihydrobenzo[g]-1,3-benzodioxolo[5,6-a]quinolizinium iodide (13-[3-(phenyl)propyl]berberine iodide)

To 393 mg (1 mmol) of acetonylberberine dissolved in 20 ml of acetonitrile were added 2.985 g (15 mmol) of 3-phenylpropylbromide and 450 mg (3 mmol) of sodium iodide. The reaction mixture was refluxed for 6 h, then concentrated under vacuum and finally purified by column chromatography with dichlorometane-methanol 4% as eluant to give 47 mg of title compound (89% yield).

NMR (200 MHz, DMSO-$d_6$) δ: 9.88 (s, 1H), 8.19 (d, 1H), 8.20 (d,1H), 7.70 (s,1H), 7.29 (s, 1H), 7.16 (s, 1H), 6.18 (s, 2H), 4.80 (m, 2H), 4.00 (s,3H), 4.20 (s, 3H), 3.10 (t, 2H), 2.50 (m, 4H)

Preparation of Formulations in Cyclodextrins

EXAMPLE 9

0.15 mmol of a compound of formula (I) and 0.38 mmol of beta-cyclodextrin are dissolved in 100 mL of water with stirring for 6 hours. The resulting product is separated by precipitation by cooling the solution at 3° C. or, alternatively, by freeze-drying the solution.

EXAMPLE 10

2.64 mmol of gamma-cyclodextrin are dissolved in 100 mL of water by applying a gentle heating. To the resulting solution there are added 1.06 mmol of a compound of formula (I) with stirring for 6-12 hours. The product is separated by precipitation by cooling the solution at 3° C. or, alternatively, by freeze-drying the solution.

EXAMPLE 11

Mixtures of a compound of formula (I) and of different amounts of beta-cyclodextrin, or gamma-cyclodextrin are prepared by grinding, followed by sieving (<0.375 mm) and 10 minute of mixing in a turbo-mixer.

What is claimed is:

1. 13-Substituted 5,6-dihydrodibenzo[a,g]quinolizinium salt compounds (13-substituted protoberberines) of the general formula (I):

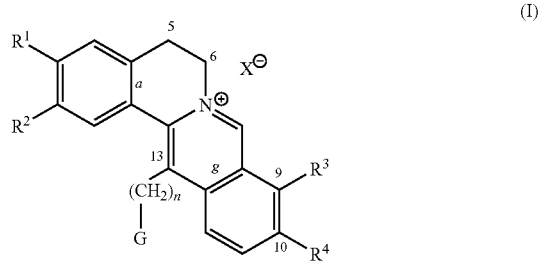

wherein;
$R^1$ and $R^2$, which may be the same or different, represent independently a hydroxy or a $(C_1-C_6)$alkoxy group, or, taken together, a methylenedioxy group;
$R^3$ and $R^4$, which may be the same or different, represent independently a hydroxy or a $(C_1-C_6)$alkoxy group;
X represents inorganic acid ion, organic acid ion or halide; and
(a) n is an integer from 1 to 5 inclusive and G stands for —Y=(Ar)$_2$ or n is an integer from 2 to 5 inclusive and G stands for —Z—Ar, in which:
Y is CH, O(CH$_2$)$_m$—CH, CO—N, CO—NH(CH$_2$)$_m$—C, or NH—CO(CH$_2$)$_m$—CH;
Z is a bond, or O(CH$_2$)$_m$, CO—NH(CH$_2$)$_m$, or NH—CO(CH$_2$)$_m$;
m is an integer from 0 to 3 inclusive; and
Ar represents a 5-15 membered unsaturated or aromatic mono-, bi- or tricyclic carbocyclic or heterocyclic ring system, wherein any of said heterocyclic ring systems, for each occurrence, contains one or more heteroatoms selected from O, N, or S; and wherein any of said ring systems, for each occurrence, optionally contains from 1 to 4 substituents independently selected from halogen, cyano, nitro, hydroxy, amino, (di)(C$_1$-C$_6$)alkylamino, (C$_1$-C$_6$)alkylcarbonylamino, (C$_1$-C$_6$)alkoxy, (C$_1$-C$_6$)alkylcarbonyloxy, (C$_1$-C$_6$)alkoxycarbonyl, (C$_1$-C$_6$)alkyl; and wherein any of said (C$_1$-C$_6$)alk* moieties, for each occurrence, contains from 1 to 4 halogen atoms independently chosen from F, Cl, Br and I, or (b) n is 1 and G stands for —Z—Ar in which:
Z is O(CH$_2$)$_m$, CO—NH(CH$_2$)$_m$, or NH—CO(CH$_2$)$_m$;
m is an integer from 0 to 3 inclusive; and
Ar represents a 5-15 membered unsaturated or aromatic mono-, bi- or tricyclic carbocyclic or heterocyclic ring system, wherein any of said heterocyclic ring systems, for each occurrence, contains one o more heteroatoms selected from O, N, or S; and
wherein any of said ring systems, for each occurrence, optionally contains from 1 to 4 substituents independently selected from halogen, cyano, nitro, hydroxy, amino, (di)(C$_1$-C$_6$)alkylamino, (C$_1$-C$_6$)alkylcarbonylamino, (C$_1$-C$_6$)alkoxy, (C$_1$-C$_6$)alkylcarbonyloxy, (C$_1$-C$_6$)alkoxycarbonyl, (C$_1$-C$_6$)alkyl; and wherein any of said (C$_1$-C$_6$)alk* moieties, for each occurrence, contains from 1 to 4 halogen atoms independently chosen from F, Cl, Br and I;
or
(c) n is 1 and G stands for —Z—Ar in which:
Z is a bond,
and
Ar represents
(i) an unsaturated or aromatic mono- or bicyclic carbocyclic ring system radical chosen from naphthyl, indenyl, azulenyl, optionally containing from 1 to 4 substituents, wherein the 1 to 4 substituents are optionally selected from the group consisting of methyl, ethyl, propyl; trifluoromethyl, trichloromethyl, tribromomethyl, 3,3,3-trifluoroethyl, 3,3,3-trichloroethyl; hydroxy, methoxy, ethoxy, 3,3,3-trichloroethoxy, acetoxy, trifluoroacetoxy, trichloroacetoxy;
amino, (di)methylamino, (di)ethylamino, acetamido, trifluoroacetamido; cyano, nitro, fluoro, chloro, iodo and bromo, or
(ii) an unsaturated or aromatic mono- or bicyclic heterocyclic ring system radical chosen from imidazolyl, quinolyl, isoquinolyl, indolyl, indazolyl, pyridazyl, pyrrolyl, pyrazolyl, pyrazinyl, quinoxalyl, pyrimidinyl, pyridazinyl, furyl, thienyl, triazolyl, thiazolyl, tetrazolyl, benzofuranoyl, oxazolyl, benzoxazolyl, isoxazolyl, isothiazolyl, thiazolyl, thiadiazoyl, benzodioxolyl, optionally containing from 1 to 4 substituents, wherein the 1 to 4 substituents are optionally selected from the group consisting of methyl, ethyl, propyl;
trifluoromethyl, trichloromethyl, tribromomethyl, 3,3,3-trifluoroethyl, 3,3,3-trichloroethyl; hydroxy, methoxy, ethoxy, 3,3,3-trichloroethoxy, acetoxy, trifluoroacetoxy, trichloroacetoxy; amino, (di)methylamino, (di)ethylamino, acetamido, trifluoroacetamido; cyano, nitro, fluoro, chloro, iodo and bromo.

2. Compounds according to claim 1, wherein $R^1$ and $R^2$ are methoxy groups, or, taken together, represent a methylenedioxy group; $R^3$ is hydroxy or methoxy; $R^4$ is methoxy.

3. Compounds according to claim 1, wherein G stands for —Z—Ar.

4. Compounds according to claim 3, wherein Z is a bond; and n is 2, 3, 4, or 5.

5. Compounds according to claim 3, wherein Z is O(CH$_2$)$_m$; m is 0, 1, or 2; and n is 1.

6. Compounds according to claim 3, wherein Z is CO—NH(CH$_2$)$_m$, or NH—CO(CH$_2$)$_m$; m is 0, 1, or 2; and n is 1.

7. Compounds according to claim 1, wherein G stands for —Y=(Ar)$_2$.

8. Compounds according to claim 7, wherein Y is CH; and n is 1, 2, 3, or 4.

9. Compounds according to claim 7, wherein Y is O (CH$_2$)$_m$—CH; m is 0 or 1; and n is 1, 2 or 3.

10. Compounds according to claim 7, wherein Y is CO—N; and n is 1.

11. Compounds according to claim 7, wherein Y is CO—NH (CH$_2$)$_m$—CH; or NH—CO(CH$_2$)$_m$—CH; m is 0 or 1; and n is 1.

12. Compounds according to claim 1, wherein for (a) or (or) b wherein Ar represents an unsaturated or aromatic mono- or bicyclic carbocyclic ring system radical chosen from phenyl, naphthyl, indenyl, azulenyl, optionally containing from 1 to 4 substituents, wherein the 1 to 4 substituents are optionally selected from the group consisting of methyl, ethyl, propyl; trifluoromethyl, trichloromethyl, tribromomethyl, 3,3,3-trifluoroethyl, 3,3,3-trichloroethyl; hydroxy, methoxy, ethoxy, 3,3,3-trichloroethoxy, acetoxy, trifluoroacetoxy, trichloroacetoxy; amino, (di)methylamino, (di)ethylamino, acetamido, trifluoroacetamido; cyano, nitro, fluoro, chloro, iodo and bromo.

13. Compounds according to claim 1, wherein for (a) or (or) b Ar represents an unsaturated or aromatic mono- or bicyclic heterocyclic ring system radical chosen from imidazolyl, quinolyl, isoquinolyl, indolyl, indazolyl, pyridazyl, pyridyl, pyrrolyl, pyrazolyl, pyrazinyl, quinoxalyl, pyrimidinyl, pyridazinyl, furyl, thienyl, triazolyl, thiazolyl, tetrazolyl, benzofuranoyl, oxazolyl, benzoxazolyl, isoxazolyl, isothiazolyl, thiazolyl, thiadiazoyl, benzodioxolyl, optionally containing from 1 to 4 substituents, wherein the 1 to 4 substituents are optionally selected from the group consisting of methyl, ethyl, propyl; trifluoromethyl, trichloromethyl, tribromomethyl, 3,3,3-trifluoroethyl, 3,3,3-trichloroethyl; hydroxy, methoxy, ethoxy, 3,3,3-trichloroethoxy, acetoxy, trifluoroacetoxy, trichloroacetoxy; amino, (di)methylamino, (di)ethylamino, acetamido, trifluoroacetamido; cyano, nitro, fluoro, chloro, iodo and bromo.

14. Compounds according to claim 3, wherein Ar is an unsaturated Or aromatic tricyclic carbocyclic or heterocyclic ring system radical chosen from fluorenyl, anthracenyl, 5H-dibenzocycloheptenyl, 10,11-dihydro-5H-dibenzocycloheptenyl, xanthenyl, acridinyl, phenothiazinyl, phenoxazinyl, carbazolyl, optionally containing from 1 to 4 substituents, wherein the 1 to 4 substituents are optionally selected from the group consisting of methyl, ethyl, propyl; trifluoromethyl, trichloromethyl, tribromomethyl, 3,3,3-trifluoroethyl, 3,3,3-trichloroethyl; hydroxy, methoxy, ethoxy, 3,3,3-trichloroethoxy, acetoxy, trifluoroacetoxy, trichloroacetoxy; amino, (di)methylamino, (di)ethylamino, acetamido, trifluoroacetamido; cyano, nitro, fluoro, chloro, iodo and bromo.

15. A compound according to claim 1, such compound being chosen among

13-[2-(phenyl)ethyl]-9,10-dimethoxy-5,6-dihydrobenzo[g]-1,3-benzodioxolo[5,6-a]quinolizinium iodide;
13-[2-(4-chlorophenyl)ethyl]-9,10-dimethoxy-5,6-dihydrobenzo[g]-1,3-benzodioxolo[5,6-a]quinolizinium iodide;
13-[2-(4-methoxyphenyl)ethyl]-9,10-dimethoxy-5,6-dihydrobenzo[g]-1,3-benzodioxolo[5,6-a]quinolizinium iodide;
13-[2-(4-methylphenyl)ethyl]-9,10-dimethoxy-5,6-dihydrobenzo[g]-1,3-benzodioxolo[5,6-a]quinolizinium iodide;
13-[2-(4-fluorophenyl)ethyl]-9,10-dimethoxy-5,6-dihydrobenzo[g]-1,3-benzodioxolo[5,6-a]quinolizinium iodide;
13-[2-(4-bromophenyl)ethyl]-9,10-dimethoxy-5,6-dihydrobenzo[g]-1,3-benzodioxolo[5,6-a]quinolizinium iodide;
13-[2-(4-trifluoromethylphenyl)ethyl]-9,10-dimethoxy-5,6-dihydrobenzo[g]-1,3-benzodioxolo[5,6-a]quinolizinium iodide;
13-[2-(4-trifluoromethoxyphenyl)ethyl]-9,10-dimethoxy-5,6-dihydrobenzo[g]-1,3-benzodioxolo[5,6-a]quinolizinium iodide;
13-[2-(4-nitrophenyl)ethyl]-9,10-dimethoxy-5,6-dihydrobenzo[g]-1,3-benzodioxolo[5,6-a]quinolizinium iodide;
13-[2-(4-dimethylaminophenyl)ethyl]-9,10-dimethoxy-5,6-dihydrobenzo[g]-1,3-benzodioxolo[5,6-a]quinolizinium iodide;
13-[2-(4-acetylaminophenyl)ethyl]-9,10-dimethoxy-5,6-dihydrobenzo[g]-1,3-benzodioxolo[5,6-a]quinolizinium iodide;
13-[2-(4-ethoxycarbonylphenyl)ethyl]-9,10-dimethoxy-5,6-dihydrobenzo[g]-1,3-benzodioxolo[5,6-a]quinolizinium iodide;
13-[2-(naphth-1-yl)ethyl]-9,10-dimethoxy-5,6-dihydrobenzo[g]-1,3-benzodioxolo[5,6-a]quinolizinium iodide;
13-[2-(4-chloronaphth-1-yl)ethyl]-9,10-dimethoxy-5,6-dihydrobenzo[g]-1,3-benzodioxolo[5,6-a]quinolizinium iodide;
13-[2-(4-methoxynaphth-1-yl)ethyl]-9,10-dimethoxy-5,6-dihydrobenzo[g]-1,3-benzodioxolo[5,6-a]quinolizinium iodide;
13-[2-(4-nitronaphth-1-yl)ethyl]-9,10-dimethoxy-5,6-dihydrobenzo[g]-1,3-benzodioxolo[5,6-a]quinolizinium iodide;
13-[2-(4-ethoxycarbonylnaphth-1-yl)ethyl]-9,10-dimethoxy-5,6-dihydrobenzo[g]-1,3-benzodioxolo[5,6-a]quinolizinium iodide;
13-[2-(indol-3-yl)ethyl]-9,10-dimethoxy-5,6-dihydrobenzo[g]-1,3-benzodioxolo[5,6-a]quinolizinium iodide;
13-[2-(5-chloroindol-3-yl)ethyl)]-9,10-dimethoxy-5,6-dihydrobenzo[g]-1,3-benzodioxolo[5,6-a]quinolizinium iodide;
13-[2-(5-nitroindol-3-yl)ethyl]-9,10-dimethoxy-5,6-dihydrobenzo[g]-1,3-benzodioxolo[5,6-a]quinolizinium iodide;
13-[2-(5-methoxyindol-3-yl)ethyl]-9,10-dimethoxy-5,6-dihydrobenzo[g]-1,3-benzodioxolo[5,6-a]quinolizinium iodide;
13-[2-(5-ethoxycarbonylindol-3-yl)ethyl]-9,10-dimethoxy-5,6-dihydrobenzo[g]-1,3-benzodioxolo[5,6-a]quinolizinium iodide;
13-[3-(phenyl)propyl]-9,10-dimethoxy-5,6-dihydrobenzo[g]-1,3-benzodioxolo[5,6-a]quinolizinium iodide;
13-[3-(4-chlorophenyl)propyl]-9,10-dimethoxy-5,6-dihydrobenzo[g]-1,3-benzodioxolo[5,6-a]quinolizinium iodide;
13-[3-(4-fluorophenyl)propyl]-9,10-dimethoxy-5,6-dihydrobenzo[g]-1,3-benzodioxolo[5,6-a]quinolizinium iodide;
13-[3-(4-bromophenyl)propyl]-9,10-dimethoxy-5,6-dihydrobenzo[g]-1,3-benzodioxolo[5,6-a]quinolizinium iodide;
13-[3-(4-methylphenyl)propyl]-9,10-dimethoxy-5,6-dihydrobenzo[g]-1,3-benzodioxolo[5,6-a]quinolizinium iodide;
13-[3-(4-methoxyphenyl)propyl]-9,10-dimethoxy-5,6-dihydrobenzo[g]-1,3-benzodioxolo[5,6-a]quinolizinium iodide;

13-[3-(4-trifluoromethoxyphenyl)propyl]-9,10-dimethoxy-5,6-dihydrobenzo[g]-1,3-benzodioxolo[5,6-a]quinolizinium iodide;
13-[3-(4-trifluoromethylphenyl)propyl]-9,10-dimethoxy-5,6-dihydrobenzo[g]-1,3-benzodioxolo[5,6-a]quinolizinium iodide;
13-[3-(4-nitrophenyl)propyl]-9,10-dimethoxy-5,6-dihydrobenzo[g]-1,3-benzodioxolo[5,6-a]quinolizinium iodide;
13-[3-(4-dimethylaminophenyl)propyl]-9,10-dimethoxy-5,6-dihydrobenzo[g]-1,3-benzodioxolo[5,6-a]quinolizinium iodide;
13-[3-(4-acetamidophenyl)propyl]-9,10-dimethoxy-5,6-dihydrobenzo[g]-1,3-benzodioxolo[5,6-a]quinolizinium iodide;
13-[3-(4-ethoxycarbonylphenyl)propyl]-9,10-dimethoxy-5,6-dihydrobenzo[g]-1,3-benzodioxolo[5,6-a]quinolizinium iodide;
13-[3-(4-phenoxyphenyl)propyl]-9,10-dimethoxy-5,6-dihydrobenzo[g]-1,3-benzodioxolo[5,6-a]quinolizinium iodide;
13[-(naphth-1-yl)propyl]-9,10-dimethoxy-5,6-dihydrobenzo[g]-1,3-benzodioxolo[5,6-a]quinolizinium iodide;
13-[3-(4-chloronahth-1-yl)propyl]-9,10-dimethoxy-5,6-dihydrobenzo[g]-1,3-benzodioxolo[5,6-a]quinolizinium iodide;
13-[3-(4-methoxynaphth-1-yl)propyl]-9,10-dimethoxy-5,6-dihydrobenzo[g]-1,3-benzodioxolo[5,6-a]quinolizinium iodide;
13-[3-(4-nitronaphth-1-yl)propyl]-9,10-dimethoxy-5,6-dihydrobenzo[g]-1,3-benzodioxolo[5,6-a]quinolizinium iodide;
13-[3-(4-carbethoxynaphth-1-yl)propyl]-9,10-dimethoxy-5,6-dihydrobenzo[g]-1,3-benzodioxolo[5,6-a]quinolizinium iodide;
13-(3-indolylpropyl)-9,10-dimethoxy-5,6-dihydrobenzo[g]-1,3-benzodioxolo[5,6-a]quinolizinium iodide;
13-[3-(5-chloroindol-3-yl)propyl]-9,10-dimethoxy-5,6-dihydrobenzo[g]-1,3-benzodioxolo[5,6-a]quinolizinium iodide;
13-[3-(5-nitroindol-3-yl)propyl]-9,10-dimethoxy-5,6-dihydrobenzo[g]-1,3-benzodioxolo[5,6-a]quinolizinium iodide;
13-[3-(5-methoxyindol-3-yl)propyl]-9,10-dimethoxy-5,6-dihydrobenzo[g]-1,3-benzodioxolo[5,6-a]quinolizinium iodide;
13[-3-(5-carbethoxyindol-3-yl)propyl]-9,10-dimethoxy-5,6-dihydrobenzo[g]-1,3-benzodioxolo[5,6-a]quinolizinium iodide;
13-[(1,4-benzodioxan-2-yl)methyl]-9,10-dimethoxy-5,6-dihydrobenzo[g]-1,3-benzodioxolo[5,6-a]quinolizinium chloride;
13-[2,2-bis(phenyl)ethyl]-9,10-dimethoxy-5,6-dihydrobenzo[g]-1,3-benzodioxolo[5,6-a]quinolizinium iodide;
13-[2,2-bis(4-chlorophenyl)ethyl]-9,10-dimethoxy-5,6-dihydrobenzo[g]-1,3-benzodioxolo[5,6-a]quinolizinium iodide;
13-[2,2-bis(4-bromophenyl)ethyl]-9,10-dimethoxy-5,6-dihydrobenzo[g]-1,3-benzodioxolo[5,6-a]quinolizinium iodide;
13-[2,2-bis(4-fluorophenyl)ethyl]-9,10-dimethoxy-5,6-dihydrobenzo[g]-1,3-benzodioxolo[5,6-a]quinolizinium iodide;
13-[2,2-bis(4-methylphenyl)ethyl]-9,10-dimethoxy-5,6-dihydrobenzo[g]-1,3-benzodioxolo[5,6-a]quinolizinium iodide;
13-[2,2-bis(4-methoxyphenyl)ethyl]-9,10-dimethoxy-5,6-dihydrobenzo[g]-1,3-benzodioxolo[5,6-a]quinolizinium iodide;
13-[3,3-bis(phenyl)propyl]-9,10-dimethoxy-5,6-dihydrobenzo[g]-1,3-benzodioxolo[5,6-a]quinolizinium iodide;
13-[3,3-bis(4-methylphenyl)propyl]-9,10-dimethoxy-5,6-dihydrobenzo[g]-1,3-benzodioxolo[5,6-a]quinolizinium iodide;
13-[3,3-bis(4-methoxyphenyl)propyl]-9,10-dimethoxy-5,6-dihydrobenzo[g]-1,3-benzodioxolo[5,6-a]quinolizinium iodide;
13-[3,3-bis(4-fluorophenyl)propyl]-9,10-dimethoxy-5,6-dihydrobenzo[g]-1,3-benzodioxolo[5,6-a]quinolizinium iodide;
13-[3,3-bis(4-chlorophenyl)propyl]-9,10-dimethoxy-5,6-dihydrobenzo[g]-1,3-benzodioxolo[5,6-a]quinolizinium iodide;
13-[3,3-bis(4-bromophenyl)propyl]-9,10-dimethoxy-5,6-dihydrobenzo[g]-1,3-benzodioxolo[5,6-a]quinolizinium iodide;
13-benzyloxymethyl-9,10-dimethoxy-5,6-dihydrobenzo[g]-1,3-benzodioxolo[5,6-a]quinolizinium iodide;
13-[2-(phenoxy)ethyl]-9,10-dimethoxy-5,6-dihydrobenzo[g]-1,3-benzodioxolo[5,6-a]quinolizinium iodide;
13-[2-(benzyloxy)ethyl]-9,10-dimethoxy-5,6-dihydrobenzo[g]-1,3-benzodioxolo[5,6-a]quinolizinium iodide;
13-[3-(phenoxy)propyl]-9,10-dimethoxy-5,6-dihydrobenzo[g]-1,3-benzodioxolo[5,6-a]quinolizinium iodide;
13-[(1,4-benzodioxan-2-yl)methyl]-9,10-dimethoxy-5,6-dihydrobenzo[g]-1,3-benzodioxolo[5,6-a]quinolizinium iodide;
13-[(4-chlorobenzyloxy)methyl]-9,10-dimethoxy-5,6-dihydrobenzo[g]-1,3-benzodioxolo[5,6-a]quinolizinium iodide;
13-[(4-methoxybenzyloxy)methyl]-9,10-dimethoxy-5,6-dihydrobenzo[g]-1,3-benzodioxolo[5,6-a]quinolizinium iodide;
13-[(4-dimethylaminobenzyloxy)methyl]-9,10-dimethoxy-5,6-dihydrobenzo[g]-1,3-benzodioxolo[5,6-a]quinolizinium iodide;
13-[(4-hydroxybenzyloxy)methyl]-9,10-dimethoxy-5,6-dihydrobenzo[g]-1,3-benzodioxolo[5,6-a]quinolizinium iodide;
13-[2-(p-chlorophenoxy)ethyl]-9,10-dimethoxy-5,6-dihydrobenzo[g]-1,3-benzodioxolo[5,6-a]quinolizinium iodide;
13-[2-(p-methoxyphenoxy)ethyl]-9,10-dimethoxy-5,6-dihydrobenzo[g]-1,3-benzodioxolo[5,6-a]quinolizinium iodide;
13-[2-(p-hydroxyphenoxy)ethyl]-9,10-dimethoxy-5,6-dihydrobenzo[g]-1,3-benzodioxolo[5,6-a]quinolizinium iodide;
13-[2-(p-chlorobenzyloxy)ethyl]-9,10-dimethoxy-5,6-dihydrobenzo[g]-1,3-benzodioxolo[5,6-a]quinolizinium iodide;
13-[2-(p-methoxybenzyloxy)ethyl]-9,10-dimethoxy-5,6-dihydrobenzo[g]-1,3-benzodioxolo[5,6-a]quinolizinium iodide;

13-[2-(p-hydroxybenzyloxy)ethyl]-9,10-dimethoxy-5,6-dihydrobenzo[g]-1,3-benzodioxolo[5,6-a]quinolizinium iodide;

13-[3-(p-chlorophenoxy)propyl]-9,10-dimethoxy-5,6-dihydrobenzo[g]-1,3-benzodioxolo[5,6-a]quinolizinium iodide;

13-[3-(p-methoxyphenoxy)propyl]-9,10-dimethoxy-5,6-dihydrobenzo[g]-1,3-benzodioxolo[5,6-a]quinolizinium iodide;

13-[3-(p-hydroxyphenoxy)propyl]-9,10-dimethoxy-5,6-dihydrobenzo[g]-1,3-benzodioxolo[5,6-a]quinolizinium iodide;

13-[2-(diphenylmethyloxy)ethyl]-9,10-dimethoxy-5,6-dihydrobenzo[g]-1,3-benzodioxolo[5,6-a]quinolizinium iodide;

13-diphenylmethyloxymethyl-9,10-dimethoxy-5,6-dihydrobenzo[g]-1,3-benzodioxolo[5,6-a]quinolizinium iodide;

13-benzylaminocarbonylmethyl-9,10-dimethoxy-5,6-dihydrobenzo[g]-1,3-benzodioxolo[5,6-a]quinolizinium iodide;

13-phenylaminocarbonylethyl-9,10-dimethoxy-5,6-dihydrobenzo[g]-1,3-benzodioxolo[5,6-a]quinolizinium iodide;

13-phenylaminocarbonylmethyl-9,10-dimethoxy-5,6-dihydrobenzo[g]-1,3-benzodioxolo[5,6-a]quinolizinium iodide;

13-[(4-pyridyl)aminocarbonylmethyl]-9,10-dimethoxy-5,6-dihydrobenzo[g]-1,3-benzodioxolo[5,6-a]quinolizinium iodide;

13-[(1-indolyl)carbonylmethyl)-9,10-dimethoxy-5,6-dihydrobenzo[g]-1,3-benzodioxolo[5,6-a]quinolizinium iodide;

13-[(p-chlorobenzyl)aminocarbonylmethyl]-9,10-dimethoxy-5,6-dihydrobenzo[g]-1,3-benzodioxolo[5,6-a]quinolizinium iodide;

13-[(p-methoxybenzyl)aminocarbonylmethyl]-9,10-dimethoxy-5,6-dihydrobenzo[g]-1,3-benzodioxolo[5,6-a]quinolizinium iodide;

13-[(p-dimethylaminobenzyl)aminocarbonylmethyl]-9,10-dimethoxy-5,6-dihydrobenzo[g]-1,3-benzodioxolo[5,6-a]quinolizinium iodide;

13-[(p-hydroxybenzyl)aminocarbonymethyl]-9,10-dimethoxy-5,6-dihydrobenzo[g]-1,3-benzodioxolo[5,6-a]quinolizinium iodide;

13-[(p-chlorophenyl)aminocarbonylmethyl]-9,10-dimethoxy-5,6-dihydrobenzo[g]-1,3-benzodioxolo[5,6-a]quinolizinium iodide;

13-[(p-methoxyphenyl)aminocarbonylmethyl]-9,10-dimethoxy-5,6-dihydrobenzo[g]-1,3-benzodioxolo[5,6-a]quinolizinium iodide;

13-[(p-dimethylaminophenyl)aminocarbonylmethyl]-9,10-dimethoxy-5,6-dihydrobenzo[g]-1,3-benzodioxolo[5,6-a]quinolizinium iodide;

13-[(p-hydroxyphenyl)aminocarbonylmethyl]-9,10-dimethoxy-5,6-dihydrobenzo[g]-1,3-benzodioxolo[5,6-a]quinolizinium iodide;

13-[(5-chloroindol-1-yl)carbonylmethyl]-9,10-dimethoxy-5,6-dihydrobenzo[g]-1,3-benzodioxolo[5,6-a]quinolizinium iodide;

13-[(5-methoxyindol-1-yl)carbonymethyl]-9,10-dimethoxy-5,6-dihydrobenzo[g]-1,3-benzodioxolo[5,6-a]quinolizinium iodide;

13-[(5-hydroxyindol-1-yl)carbonylmethyl]-9,10-dimethoxy-5,6-dihydrobenzo[g]-1,3-benzodioxolo[5,6-a]quinolizinium iodide;

13-[(5-dimethylaminoindol-1-yl)carbonylmethyl]-9,10-dimethoxy-5,6-dihydrobenzo[g]-1,3-benzodioxolo[5,6-a]quinolizinium iodide;

13-benzylcarbonylaminomethyl-9,10-dimethoxy-5,6-dihydrobenzo[g]-1,3-benzodioxolo[5,6-a]quinolizinium iodide;

13-phenylcarbonylaminomethyl-9,10-dimethoxy-5,6-dihydrobenzo[g]-1,3-benzodioxolo[5,6-a]quinolizinium iodide;

13-[(4-pyridyl)carbonylaminomethyl]-9,10-dimethoxy-5,6-dihydrobenzo[g]-1,3-benzodioxolo[5,6-a]quinolizinium iodide;

13-[(p-chlorobenzyl)carbonylaminomethyl]-9,10-dimethoxy-5,6-dihydrobenzo[g]-1,3-benzodioxolo[5,6-a]quinolizinium iodide;

13-[(p-methoxybenzyl)carbonylaminomethyl]-9,10-dimethoxy-5,6-dihydrobenzo[g]-1,3-benzodioxolo[5,6-a]quinolizinium iodide;

13-[(p-hydroxybenzyl)carbonylaminomethyl]-9,10-dimethoxy-5,6-dihydrobenzo[g]-1,3-benzodioxolo[5,6-a]quinolizinium iodide;

13-[(p-chlorophenyl)carbonylaminomethyl]-9,10-dimethoxy-5,6-dihydrobenzo[g]-1,3-benzodioxolo[5,6-a]quinolizinium iodide;

13-[(p-methoxyphenyl)carbonylaminomethyl]-9,10-dimethoxy-5,6-dihydrobenzo[g]-1,3-benzodioxolo[5,6-a]quinolizinium iodide;

and

13-[(p-hydroxyphenyl)carbonylaminomethyl]-9,10-dimethoxy-5,6-dihydrobenzo[g]-1,3-benzodioxolo[5,6-a]quinolizinium iodide.

16. Process for preparing a compound of formula (I) of claim 1 comprising reacting a 13-substituted tetrahydroprotoberberine of general formula (II)

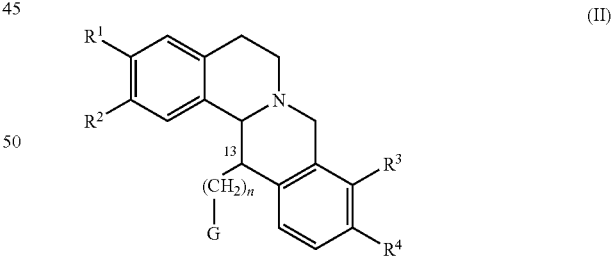

with such oxidizing agents as represented by halogens, e.g. $B_{r2}$ or $I_2$, or haloamides and haloimides, e.g N-chloro-, N-bromo- or N-iodosuccinimide to give a compound of the general formula (I) wherein X represents the halogen atom derived from the above oxidizing agent used, which process is further characterized in that:

i) when G stands for —Z—Ar, wherein Z is a bond or $O(CH_2)_m$, or for —Y=(Ar)$_2$, wherein Y is CH or $O(CH_2)_m$—CH, reacting a dihydroprotoberberine of general formula (III)

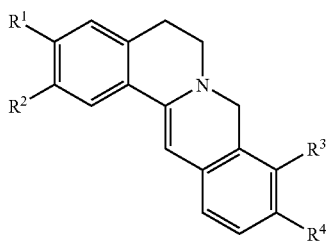
(III)

with an halide of general formulae (IVa) or (IVb)

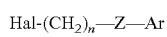
Hal—(CH$_2$)$_n$—Z—Ar  (IVa)

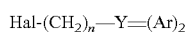
Hal—(CH$_2$)$_n$—Y=(Ar)$_2$  (IVb)

wherein:

$R^1$, $R^2$, $R^3$, $R^4$, Ar, n and m are as previously defined, Z and Y are as herein above stated, and Hal is an halogen atom such as chlorine, bromine and iodine, to give a 13-substituted iminiumprotoberberine derivative of formula (V)

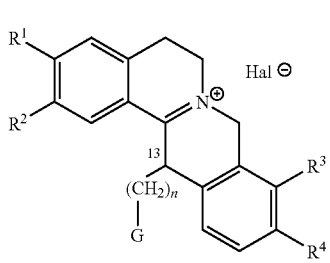
(V)

wherein $R^1$, $R^2$, $R^3$, $R^4$, n are as previously defined, and G is as herein Above stated, and reducing the 13-substituted iminiumprotoberberine of formula (V) to obtain a 13-substituted tetrahydroprotoberberine of the general formula (II-i)

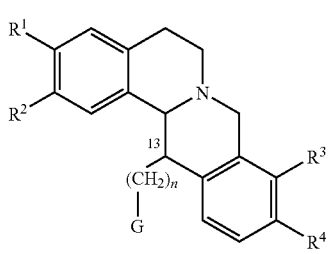
(II-i)

wherein $R^1$, $R^2$, $R^3$, $R^4$, n are as previously defined, and G is as herein Above stated;

ii) when G stands for —Z—Ar, wherein Z is CO—NH (CH$_2$)$_m$, or for —Y=(Ar)$_2$,
wherein Y is CO—N or CO—NH(CH$_2$)$_m$—CH, reacting a dihydroprotoberberine of the general formula (III) with a haloalkanoic acid ester of formula (VI)

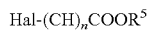
Hal—(CH)$_n$COOR$^5$  (VI)

wherein Hal and n are as previously defined, and $R^5$ represents such radicals as methyl, ethyl, t-butyl, benzyl, 2,2,2-trichloethyl and the like, to obtain an 13-alkylcarboxy acid ester iminiumprotoberberine derivative of formula (VII),

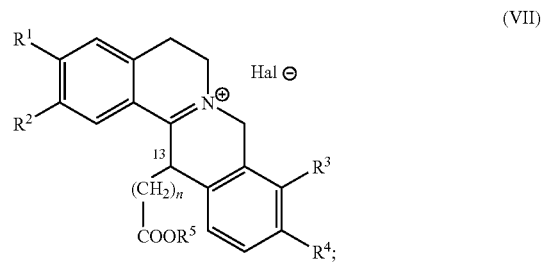
(VII)

reducing the 13-substituted iminiumprotoberberine of formula (VII) to obtain the tetrahydroprotoberberine of formula (VIII)

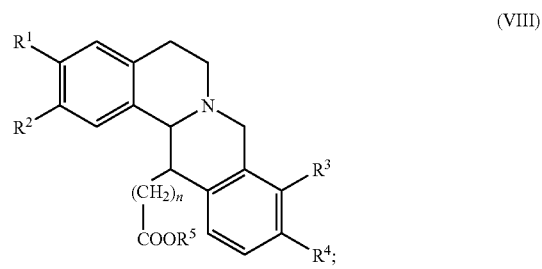
(VIII)

hydrolyzing or cleaving the ester group of the compound of formula (VIII) to obtain a 13-alkylcarboxy acid tetrahydroprotoberberine derivative of the general formula (IX)

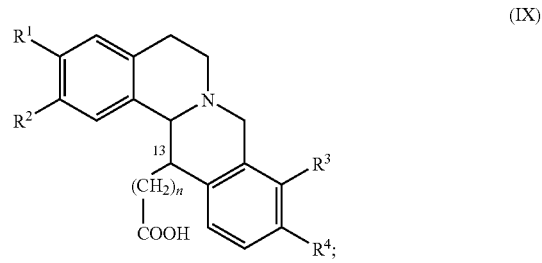
(IX)

subjecting the acid compound (IX) so obtained to an amidation reaction with an amine compound of formulae (X), (XI), or (XII)

H$_2$N(CH$_2$)$_m$—Ar  (X)

HN(Ar)$_2$  (XI)

H$_2$N(CH$_2$)$_m$—CH(Ar)$_2$  (XII)

wherein Ar and m are as previously defined to obtain a 13-substituted tetrahydroprotoberberine of the general formula (II-ii)

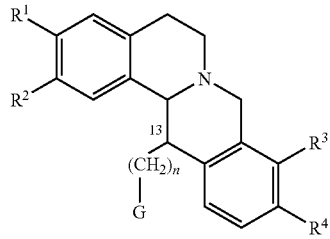
(II-ii)

wherein $R^1$, $R^2$, $R^3$, $R^4$, n are as previously defined, and G is as herein Above stated;

iii) when G stands for —Z—Ar, wherein Z is NH—CO$(CH_2)_m$, or for —Y=(Ar)$_2$, wherein Y is CO—N or NH—CO$(CH_2)_m$—CH, obtaining the acyl azido derivative of formula (XIII)

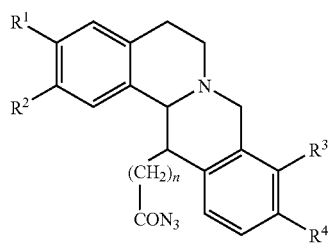
(XIII)

from the corresponding 13-alkylcarboxy acid tetrahydroprotoberberine derivative of the above general formula (IX), and subjecting the acyl azido derivative of formula (XIII) so obtained to a retro-amidation reaction with an acid compound of formulae (XIV), (XV), or (XVI)

$HOOC(CH_2)_m$—Ar  (XIV)

$HOOCCH(Ar)_2$  (XV)

$HOOC(CH_2)_m$—$CH(Ar)_2$  (XVI)

wherein Ar and m are as previously defined to obtain a 13-substituted tetrahydroprotoberberine of the general formula (II-iii)

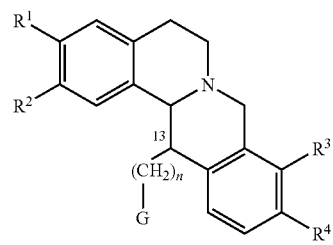
(II-iii)

wherein $R^1$, $R^2$, $R^3$, $R^4$, n are as previously defined, and G is as herein Above stated.

17. Pharmaceutical composition comprising a therapeutically effective amount of a compound according to claim 1, and a pharmaceutically acceptable carrier, adjuvant or vehicle.

18. Pharmaceutical composition of claim 17, wherein the pharmaceutically acceptable carrier, adjuvant or vehicle is alpha-, beta-, or gamma-cyclodextrin.

19. A Method for treating cancer in a mammal comprising administering a therapeutically effective amount of a compound according to claim 1 to the mammal.

20. A Method for treating cancer in a mammal comprising administering a pharmaceutical composition according to claim 17 to the mammal.

\* \* \* \* \*